US009856299B2

(12) United States Patent
Odani et al.

(10) Patent No.: US 9,856,299 B2
(45) Date of Patent: *Jan. 2, 2018

(54) USE OF IMMUNESUPPRESSANT RECEPTOR

(71) Applicant: ONO PHARMACEUTICAL CO., LTD., Osaka (JP)

(72) Inventors: Tomoyuki Odani, Osaka (JP); Hideaki Tada, Tsukuba (JP); Kimiho Yamada, Mishima-gun (JP)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/566,078

(22) Filed: Dec. 10, 2014

(65) Prior Publication Data

US 2015/0093383 A1 Apr. 2, 2015

Related U.S. Application Data

(60) Continuation of application No. 13/661,717, filed on Oct. 26, 2012, now Pat. No. 8,945,557, which is a division of application No. 12/870,508, filed on Aug. 27, 2010, now Pat. No. 8,333,969, which is a continuation of application No. 11/666,015, filed as application No. PCT/JP2005/019272 on Oct. 20, 2005, now Pat. No. 7,910,697.

(30) Foreign Application Priority Data

Oct. 21, 2004 (JP) ................................ 2004-307331

(51) Int. Cl.
| | |
|---|---|
| *A61K 38/17* | (2006.01) |
| *A61K 39/395* | (2006.01) |
| *C07K 14/47* | (2006.01) |
| *A61K 31/7088* | (2006.01) |
| *C07K 16/28* | (2006.01) |
| *G01N 33/68* | (2006.01) |
| *A61K 45/06* | (2006.01) |
| *C07K 16/18* | (2006.01) |
| *A61K 39/00* | (2006.01) |

(52) U.S. Cl.
CPC .......... *C07K 14/47* (2013.01); *A61K 31/7088* (2013.01); *A61K 38/1709* (2013.01); *A61K 38/1774* (2013.01); *A61K 39/3955* (2013.01); *A61K 45/06* (2013.01); *C07K 16/18* (2013.01); *C07K 16/28* (2013.01); *G01N 33/6854* (2013.01); *A61K 2039/505* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 7,083,793 | B2 | 8/2006 | Fraser |
| 2004/0185045 | A1 | 9/2004 | Koenig et al. |
| 2005/0164307 | A1 | 7/2005 | Kojima et al. |

FOREIGN PATENT DOCUMENTS

| | | |
|---|---|---|
| WO | 99/33873 A1 | 7/1999 |
| WO | 00/50443 A2 | 8/2000 |

OTHER PUBLICATIONS

Notice of Reasons for Refusal, dated Nov. 16, 2015, issued by the Japanese Patent Office in counterpart Japanese Patent Application No. 2014-236726.
Extended European Search Report dated Jun. 2, 2009.
Jay C Unkeless et al., "Inhibitory Receptors, ITIM Sequences and Phosphatases", Current Opinion in Immunology, Jun. 1, 1997, pp. 338-343, vol. 9, No. 3.
Communication from the Japanese Patent Office dated May 20, 2014, in a counterpart Japanese application No. 2013-061588.
Heldin et al., Cell. Jan. 27, 1995; 80(2):213-223.
European Search Report, dated Oct. 21, 2016, issued by the European Patent Office in counterpart European Patent Application No. 16182795.1.
Ravetch et al; "Immune Inhibitory Receptors," Science, Oct. 6, 2000, 290(5489): pp. 84-89.
Okazaki et al; "PD-1 Immunoreceptor inhibits B cell receptor-mediated signaling by recruiting src homology 2-domain-containing tyrosine phosphatase 2 to phosphotyrosine," Proceedings of the National Academy of Sciences, Nov. 20, 2001, 98(24): pp. 13866-13871.

*Primary Examiner* — Daniel C Gamett
(74) *Attorney, Agent, or Firm* — Sughrue Mion, PLLC

(57) ABSTRACT

The present invention relates to use of an antagonist of BIR1 (B cell immunoglobulin receptor 1) related to the present invention, a method for screening the antagonist, in addition to subtype polypeptides of BIR1, the polynucleotide encoding them and antibodies for the polypeptides.
BIR1 functions as an immunosuppressive receptor, and the antagonist of BIR1 has immunopotentive activity, which is able to use for preventing and/or treating a cancer, an immunodeficiency disease or an infectious disease.

17 Claims, 6 Drawing Sheets

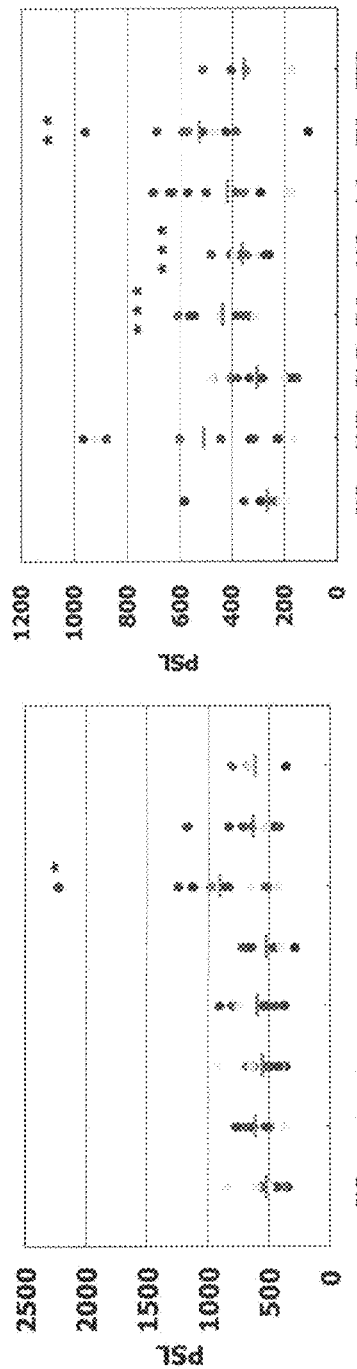
FIG. 3
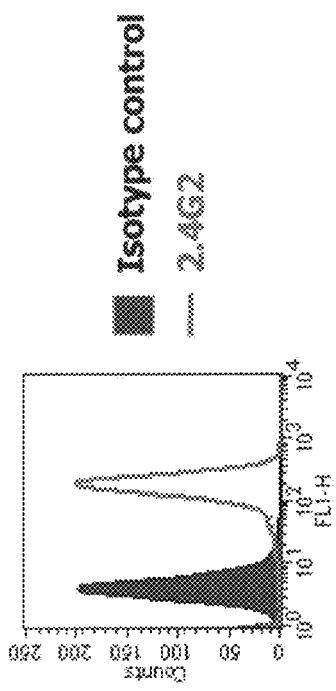
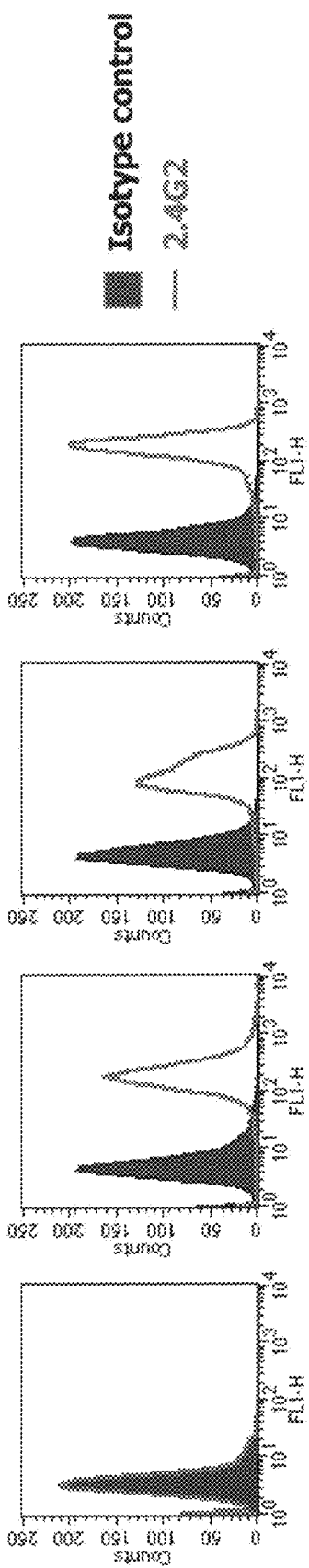
FIG. 4

USE OF IMMUNESUPPRESSANT RECEPTOR

CROSS-REFERENCE TO RELATED APPLICATIONS

This Application is a Continuation of U.S. application Ser. No. 13/661,717 filed Oct. 26, 2012, (now allowed) which is a Divisional of U.S. application Ser. No. 12/870,508, filed Aug. 27, 2012 (now allowed); which is a Continuation of U.S. patent application Ser. No. 11/666,015, filed Apr. 23, 2007 (now U.S. Pat. No. 7,910,697), which is a National Stage Application filed under §371 of PCT Application No. PCT/JP2005/019272 filed Oct. 20, 2005, which claims priority from JP 2004-307331 filed Oct. 21, 2004. The entire disclosures of the prior applications are considered part of the disclosure of the Divisional application and are hereby incorporated by reference in their entireties.

TECHNICAL FIELD

The present invention relates to use of an antagonist of the immunosuppressive receptor related to the present invention. Specifically, the present invention relates to an immunopotentiator comprising the antagonist thereof and a method for screening the antagonist.

BACKGROUND OF THE INVENTION

It is known that molecules which function as immunosuppressive receptors includes CTLA-4 (*N. Engl. J. Med.,* 338(25): 1813-21 (1998)), PD-1 (*Proc. Natl. Acad. Sci. USA,* 98(24): 13866-71 (2001)), FcγRIIB (*Science,* 290 (5489): 84-9 (2000)) and the like.

An amino acid sequence of the protein related to the present invention (sometimes referred to as B cell immunoglobulin receptor 1 (BIR1) hereinafter) and a nucleotide sequence of DNA encoding it are reported in WO 99/33873 pamphlet. However, not only functions of the protein related to the present invention are not sufficiently elucidated, uses of antagonists and agonists thereof are not known at all.

[Non-patent Reference 1] *N. Engl. J. Med.,* 338(25): 1813-21 (1998)

[Non-patent Reference 2] *Proc. Natl. Acad. Sci. USA,* 98(24): 13866-71 (2001)

[Non-patent Reference 3] *Science,* 290(5489): 84-9 (2000)

[Patent Reference 1] WO 99/33873 pamphlet

DISCLOSURE OF THE INVENTION

Problems that the Invention is to Solve

Problems of the present invention are to elucidate functions of the receptor related to the present invention and to find uses of antagonists or agonists.

Means for Solving the Problems

In order to solve the problems, the inventors of the present application have conducted intensive studies and, as a result, elucidated for the first time that the receptor related to the present invention functions as an immunosuppressive receptor, and have found respective uses of antagonists and agonists. The inventors of the present application also found a method for screening the antagonists and agonists, thereby accomplishing the present invention.

Namely, the present invention relates to (1) an immunopotentiator which comprises an antagonist of a protein having an amino acid sequence identical to or substantially identical to an amino acid sequence selected from the amino acid sequences represented by SEQ ID NOs:1 to 6, (2) the immunopotentiator according to the aforementioned (1), wherein the antagonist is a substance which attenuates or inhibits suppression of intracellular signal transduction by the protein described in the aforementioned (1), (3) the immunopotentiator according to the aforementioned (2), wherein the substance described in the aforementioned (2) is a substance which inhibits a ligand bond of the protein described in the aforementioned (1), (4) the immunopotentiator according to the aforementioned (2), wherein the substance described in the aforementioned (2) is a substance which inhibits binding of a phosphatase to an intracellular region of the protein described in the aforementioned (1), (5) the immunopotentiator according to the aforementioned (2), wherein the substance described in the aforementioned (2) is a substance which inhibits phosphatase activity, (6) the agent according to the aforementioned (3), wherein the substance which inhibits a ligand bond is a protein or polypeptide comprising an optional region in the extracellular region of the protein described in the aforementioned (1) or an antibody therefor, (7) the immunopotentiator according to the aforementioned (6), wherein the aforementioned protein or polypeptide described in (6) is a protein or polypeptide comprising an amino acid sequence identical to or substantially identical to an amino acid sequence selected from amino acids 1 to 227 in the amino acid sequence represented by SEQ ID NO:1, amino acids 1 to 227 in the amino acid sequence represented by SEQ ID NO:2, amino acids 1 to 132 in the amino acid sequence represented by SEQ ID NO:3, amino acids 1 to 137 in the amino acid sequence represented by SEQ ID NO:4, amino acids 1 to 42 in the amino acid sequence represented by SEQ ID NO:5 and amino acids 1 to 132 in the amino acid sequence represented by SEQ ID NO:6, (8) the immunopotentiator according to the aforementioned (4) or (5), wherein the phosphatase is SHP-1, SHP-2, SHIP-1 and/or SHIP-2, (9) the immunopotentiator according to the aforementioned (1), which is an agent for preventing and/or treating a disease selected from a cancer, an immunodeficiency disease and an infectious disease,

(10) A method for screening an antagonist of a protein having an amino acid sequence identical to or substantially identical to an amino acid sequence selected from the amino acid sequences represented by SEQ ID NOs:1 to 6, which comprises:

(i) allowing a protein or polypeptide comprising its extracellular region to contact with a ligand in the presence of a compound to be tested;

(ii) detecting a signal which is changed by the binding of the protein or polypeptide comprising its extracellular region with the ligand; and (iii) screening a compound which inhibits the binding, by comparing signal strengths (ii) in the presence and absence of the compound to be tested,

(11) A method for screening an antagonist of a protein having an amino acid sequence identical to or substantially identical to an amino acid sequence selected from the amino acid sequences represented by SEQ ID NOs:1 to 6, which comprises:

(i) allowing a protein or polypeptide comprising its intracellular region to contact with a phosphatase in the presence of a compound to be tested;

(ii) detecting a signal which is changed by the binding of the protein or polypeptide comprising its intracellular region with the phosphatase; and (iii) screening a compound which inhibits the binding, by comparing signal strengths in (ii) in the presence and absence of the compound to be tested,

(12) A method for screening an antagonist of a protein having an amino acid sequence identical to or substantially identical to an amino acid sequence selected from the amino acid sequences represented by SEQ ID NOs:1 to 6, which comprises:

(i) allowing a cell capable of expressing a protein having an amino acid sequence identical to or substantially identical to an amino acid sequence selected from the amino acid sequences represented by SEQ ID NOs:1 to 6, or a protein or polypeptide comprising its extracellular region, to contact with a cell capable of expressing a ligand, or the ligand, in the presence of a compound to be tested;

(ii) detecting a signal which is changed by the contact in (ii); and (iii) comparing signal strengths of the step (ii) in the presence and absence of the compound to be tested,

(13) A method for immunopotentiation, which comprises administering to a mammal an effective amount of an antagonist of a protein having an amino acid sequence identical to or substantially identical to an amino acid sequence selected from the amino acid sequences represented by SEQ ID NOs:1 to 6,

(14) use of an antagonist of a protein having an amino acid sequence identical to or substantially identical to an amino acid sequence selected from the amino acid sequences represented by SEQ ID NOs:1 to 6, for producing an immunopotentiator,

(15) a method for preventing and/or treating a disease selected from a cancer, an immunodeficiency disease and an infectious disease, which comprises administering to a mammal an effective amount of an antagonist of a protein having an amino acid sequence identical to or substantially identical to an amino acid sequence selected from the amino acid sequences represented by SEQ ID NOs:1 to 6,

(16) use of an antagonist of a protein having an amino acid sequence identical to or substantially identical to an amino acid sequence selected from the amino acid sequences represented by SEQ ID NOs:1 to 6, for producing an agent for preventing and/or treating a disease selected from a cancer, an immunodeficiency disease and an infectious disease,

(17) a protein having an amino acid sequence identical to or substantially identical to one amino acid sequence selected from the amino acid sequences represented by SEQ ID NOs:3 to 6, or a partial peptide thereof,

(18) a polynucleotide which encodes a protein having an amino acid sequence identical to or substantially identical to one amino acid sequence selected from the amino acid sequences represented by SEQ ID NOs:3 to 6, or a partial peptide thereof,

(19) an antibody for a protein having an amino acid sequence identical to or substantially identical to one amino acid sequence selected from the amino acid sequences represented by SEQ ID NOs:3 to 6, or a partial peptide thereof,

(20) an immunosuppressant, which comprises an agonist of a protein having an amino acid sequence identical to or substantially identical to an amino acid sequence selected from the amino acid sequences represented by SEQ ID NOs:1 to 6,

(21) the agent according to the aforementioned (20), wherein the agonist is a substance which keeps or reinforces suppression of intracellular signal transduction by the protein described in the aforementioned (20),

(22) the agent according to the aforementioned (21), wherein the substance described in the aforementioned (21) is a substance which cross-links the protein described in the aforementioned (20) with a receptor expressed in a cell which expresses the protein,

(23) the agent according to the aforementioned (21), wherein the substance described in the aforementioned (21) is an agonist antibody for the protein described in the aforementioned (20),

(24) the agent according to the aforementioned (20), which is an agent for preventing and/or treating a disease selected from an autoimmune disease, a rejection reaction after organ transplantation, an allergic disease and an inflammatory disease,

(25) the agent according to the aforementioned (24), wherein the autoimmune disease is a disease having high value of lupus anticoagulation factor, systemic lupus erythematodes, articular rheumatism, multiple sclerosis or Takayasu arteritis,

(26) a method for immunosuppression, which comprises administering to a mammal an effective amount of an agonist of a protein having an amino acid sequence identical to or substantially identical to an amino acid sequence selected from the amino acid sequences represented by SEQ ID NOs:1 to 6,

(27) use of an agonist of a protein having an amino acid sequence identical to or substantially identical to an amino acid sequence selected from the amino acid sequences represented by SEQ ID NOs:1 to 6, for producing an immunosuppressant,

(28) a method for preventing and/or treating a disease selected from an autoimmune disease, a rejection reaction after organ transplantation, an allergic disease and an inflammatory disease, which comprises administering to a mammal an effective amount of an agonist of a protein having an amino acid sequence identical to or substantially identical to an amino acid sequence selected from the amino acid sequences represented by SEQ ID NOs:1 to 6, and

(29) use of an agonist of a protein having an amino acid sequence identical to or substantially identical to an amino acid sequence selected from the amino acid sequences represented by SEQ ID NOs:1 to 6, for producing an agent for preventing and/or treating a disease selected from an autoimmune disease, a rejection reaction after organ transplantation, an allergic disease and an inflammatory disease.

Effect of the Invention

The antagonist of the protein related to the present invention is expected to have effect to prevent and/or treat a cancer, an immunodeficiency disease or an infectious disease. The agonist of the protein related to the present invention is also expected to have effect to prevent and/or treat an autoimmune disease, a rejection reaction after organ transplantation, an allergic disease or an inflammatory disease.

BEST MODE FOR CARRYING OUT THE INVENTION

According to the description of the present invention, the "protein having substantially identical amino acid sequence" in the "protein having an amino acid sequence identical to or substantially identical to an amino acid sequence selected from the amino acid sequences represented by SEQ ID NOs:1 to 6" means a protein having the same function of the protein having an amino acid sequence selected from the amino acid sequences represented by SEQ ID NOs:1 to 6, in which several amino acids (preferably from 1 to 5 residues, more preferably 1 or 2 residues) of the amino acids selected from the amino acid sequences represented by SEQ ID NOs:1 to 6 are deleted, several amino acids (preferably from 1 to 5 residues, more preferably 1 or 2 residues) therein are substituted with other amino acids, or several residues of amino acids (preferably from 1 to 5 residues, more preferably 1 or 2 residues) are added to or inserted into the amino acid sequence, or which has an amino acid sequence of the combination therewith. In this case, the position of the aforementioned deletion, substitution or addition or insertion of amino acids is not particularly limited. Hereinafter, the "protein having an amino acid sequence identical to or substantially identical to an amino acid sequence selected from the amino acid sequences represented by SEQ ID NOs:1 to 6" as used in the specification of the present invention may be called "the protein related to the present invention" in some cases.

In this connection, the protein related to the present invention is preferably a protein having an amino acid sequence identical to or substantially identical to an amino acid sequence selected from the amino acid sequences represented by SEQ ID NOs:1 to 4 and SEQ ID NO:6, more preferably a protein having an amino acid sequence identical to or substantially identical to an amino acid sequence selected from the amino acid sequences represented by SEQ ID NOs:1 to 4, further preferably a protein having an amino acid sequence identical to or substantially identical to an amino acid sequence selected from the amino acid sequences represented by SEQ ID NO:1 or 2, and still further preferably a protein having the amino acid sequence represented by SEQ ID NO:1 or 2.

According to the specification of the present invention, the "antagonist of a protein having an amino acid sequence identical to or substantially identical to an amino acid sequence selected from the amino acid sequences represented by SEQ ID NOs:1 to 6" represents a substance which attenuates or inhibits suppression of intracellular signal transduction by the protein related to the present invention. Such a substance includes (i) a substance which inhibits ligand binding to the protein related to the present invention and does not have agonist activity for the protein related to the present invention;

(ii) a substance which inhibits binding of a phosphatase to the intracellular region of the protein related to the present invention;

(iii) a substance which inhibits activity of the phosphatase; and (iv) a substance which inhibits activity of a phosphatase bound to the intracellular region of the protein related to the present invention; and the like.

In this case, the "intracellular signal" includes, intracellular signals generated from B cell receptor (BCR) or B cell receptor complexes (BCR, CD79A (*EMBO J.*, 7(11): 3457-3464 (1988)) and CD79B (*Eur. J. Immunol.*, 22(6): 1621-1625 (1992))), activated Fc receptors (e.g., FcγRI (*J. Biol. Chem.*, 266(20): 13449-13455 (1991))), CD14/TLR4 complex (*Nature*, 406: 780-785 (2000)), FcεRI (*Proc. Natl. Acad. Sci. USA*, 85: 1907-1911 (1988)) and the like. Additionally, the "suppression of intracellular signal transduction by the protein related to the present invention" includes, for example, dephosphorylation of an intracellular signal transduction-carrying molecule by a phosphatase bound to the intracellular region of the protein related to the present invention.

In this case, the "substance which inhibits ligand bond to the protein related to the present invention and does not have agonist activity for the protein related to the present invention" includes, for example, a protein, a polypeptide or peptide, an antibody, a non-peptide compound, an organic synthesis compound or natural product (e.g., a fermentation product, a cell extract, a plant extract, an animal tissue extract or the like) and the like.

Preferred as such a substance is a protein, a polypeptide or an antibody, and its illustrative examples include a protein or polypeptide comprising an optional region in the extracellular region of the protein related to the present invention and an antibody for the same and the like.

The "protein or polypeptide comprising an optional region in the extracellular region of the protein related to the present invention" is a protein or polypeptide which contains an optional region in the extracellular region of the protein related to the present invention, which does not contain transmembrane region and intracellular region. Specifically, it is a protein or polypeptide which contains a region optionally selected from the region of amino acids 1 to 227 in the amino acid sequence represented by SEQ ID NO:1, a region optionally selected from the region of amino acids 1 to 227 in the amino acid sequence represented by SEQ ID NO:2, a region optionally selected from the region of amino acids 1 to 132 in the amino acid sequence represented by SEQ ID NO:3, a region optionally selected from the region of amino acids 1 to 137 in the amino acid sequence represented by SEQ ID NO:4, a region optionally selected from the region of amino acids 1 to 42 in the amino acid sequence represented by SEQ ID NO:5 or a region optionally selected from the region of amino acids 1 to 132 in the amino acid sequence represented by SEQ ID NO:6, and which does not contain transmembrane region and intracellular region. The "transmembrane region" is a region of amino acids 228 to 250 in the amino acid sequence represented by SEQ ID NO:1, a region of amino acids 228 to 250 in the amino acid sequence represented by SEQ ID NO:2, a region of amino acids 133 to 155 in the amino acid sequence represented by SEQ ID NO:3, a region of amino acids 138 to 160 in the amino acid sequence represented by SEQ ID NO:4, a region of amino acids 43 to 65 in the amino acid sequence represented by SEQ ID NO:5 or a region of amino acids 133 to 155 in the amino acid sequence represented by SEQ ID NO:6, and the "intracellular region" is a region of amino acids 251 to 343 of the amino acid sequence represented by SEQ ID NO:1, a region of amino acids 251 to 343 in the amino acid sequence represented by SEQ ID NO:2, a region of amino acids 156 to 248 in the amino acid sequence represented by SEQ ID NO:3, a region of amino acids 161 to 253 in the amino acid sequence represented by SEQ ID NO:4, a region of amino acids 66 to 158 in the amino acid sequence represented by SEQ ID NO:5 or a region of amino acids 156 to 176 in the amino acid sequence represented by SEQ ID NO:6.

Those which are fused with other protein or polypeptide are also included in the protein or polypeptide containing an optional region in the extracellular region of the protein related to the present invention. Examples include those which are fused with the Fc domain of immunoglobulin for the solubilization of the protein or polypeptide and the like, and they can be produced by conventionally known methods.

The "optional region" in the "protein or polypeptide containing an optional region in the extracellular region of the protein related to the present invention" may be any region in the extracellular region of the protein related to the present invention, so long as it has the antagonist activity for the protein related to the present invention.

These proteins or polypeptides also include, for example, those in which several amino acids (preferably from 1 to 5 residues, more preferably 1 or 2 residues) in the protein or polypeptide are deleted, several amino acids (preferably from 1 to 5 residues, more preferably 1 or 2 residues) therein are substituted with other amino acids, or several amino acids (preferably from 1 to 5 residues, more preferably 1 or 2 residues) are added to or inserted into the amino acid sequence, or which have an amino acid sequence of the combination thereof, for the purpose of keeping or improving the antagonist activity, stabilizing the protein or polypeptide or reducing antigenicity.

The protein or polypeptide containing an optional region in the extracellular region of the protein related to the present invention can be prepared by conventionally known protein expression methods and purification methods or by the methods described in Examples.

The "ligand" in the "ligand bond of the protein related to the present invention" is an intravital substance which binds to the extracellular region of the protein related to the present invention and has the activity to induce functions of the protein related to the present invention. A protein is preferred as such a ligand. The "extracellular region of the protein related to the present invention" is a region which comprises a domain so-called immunoglobulin or immunoglobulin-like domain, and is a region of amino acids 1 to 227 in the amino acid sequence represented by SEQ ID NO:1, a region of amino acids 1 to 227 in the amino acid sequence represented by SEQ ID NO:2, a region of amino acids 1 to 132 in the amino acid sequence represented by SEQ ID NO:3, a region of amino acids 1 to 137 in the amino acid sequence represented by SEQ ID NO:4, a region of amino acids 1 to 42 in the amino acid sequence represented by SEQ ID NO:5 or a region of amino acids 1 to 132 in the amino acid sequence represented by SEQ ID NO:6.

The term "does not have agonist activity for the protein related to the present invention" means that it does not have any activity which stimulates functions of the protein related to the present invention.

The "intracellular region of the protein related to the present invention" is specifically a region of amino acids 251 to 343 in the amino acid sequence represented by SEQ ID NO:1, a region of amino acids 251 to 343 in the amino acid sequence represented by SEQ ID NO:2, a region of amino acids 156 to 248 in the amino acid sequence represented by SEQ ID NO:3, a region of amino acids 161 to 253 in the amino acid sequence represented by SEQ ID NO:4, a region of amino acids 66 to 158 in the amino acid sequence represented by SEQ ID NO:5 or a region of amino acids 156 to 176 in the amino acid sequence represented by SEQ ID NO:6. So-called ITIM (immunoreceptor tyrosine-based inhibitory motif)-like domain is present in the intracellular region of the protein related to the present invention, which, specifically, is present in amino acids 311 to 316 and/or 336 to 341 in the amino acid sequence represented by SEQ ID NO:1, amino acids 311 to 316 and/or 336 to 341 in the amino acid sequence represented by SEQ ID NO:2, amino acids 216 to 221 and/or 241 to 246 in the amino acid sequence represented by SEQ ID NO:3, amino acids 221 to 226 and/or 246 to 251 in the amino acid sequence represented by SEQ ID NO:4, amino acids 126 to 131 and/or 151 to 156 in the amino acid sequence represented by SEQ ID NO:5 or amino acids 169 to 174 in the amino acid sequence represented by SEQ ID NO:6.

The "phosphatase" in the "substance which inhibits binding of a phosphatase to the intracellular region of the protein related to the present invention", the "substance which inhibits the phosphatase activity" or the "substance which inhibits activity of a phosphatase bound to the intracellular region of the protein related to the present invention", includes, for example, phosphatases called SHP-1 (*Nature*, 352(6337): 736-739 (1991)), SHP-2 (*Proc. Natl. Acad. Sci.*, 90: 2197-2201 (1993)), SHIP-1 (*Proc. Natl. Acad. Sci.*, 93: 1689-1693 (1996)), SHIP-2 (*Biochem. Biophys. Res. Commun.*, 239(3): 697-700 (1997)) and the like.

The "binding of a phosphatase to the intracellular region" in the "substance which inhibits binding of a phosphatase to the intracellular region of the protein related to the present invention" is the binding of a phosphatase to the ITIM-like domain, and the binding requires phosphorylation of certain tyrosine residues contained in the ITIM-like domain. Such tyrosine residues is amino acid 313th position and 338th position tyrosine residues in the amino acid sequence represented by SEQ ID NO:1, amino acid 313th position and 338th position tyrosine residues in the amino acid sequence represented by SEQ ID NO:2, amino acid 218th position and 243th position tyrosine residues in the amino acid sequence represented by SEQ ID NO:3, amino acid 223th position and 248th position tyrosine residues in the amino acid sequence represented by SEQ ID NO:4, amino acid 128th position and 153th position tyrosine residues in the amino acid sequence represented by SEQ ID NO:5 or amino acid 171th position tyrosine residue in the amino acid sequence represented by SEQ ID NO:6.

The target to be dephosphorylated by the phosphatase in the "substance which inhibits the phosphatase activity" or the "substance which inhibits activity of a phosphatase bound to the intracellular region of the protein related to the present invention" includes, for example, intracellular signal transducer molecules such as a kinase, an inositol phosphate and the like. The kinase includes, for example, a serine/threonine kinase (e.g., protein kinase A, protein kinase C, $Ca^{2+}$/calmodulin dependent protein kinase, MAP kinase, Mos/Raf kinase or the like), a tyrosine kinase (e.g., receptor type tyrosine kinase, non-receptor type tyrosine kinase or the like) and the like. The inositol phosphate includes, for example, phosphatidylinositol-3,4,5-triphosphate and the like.

The target kinase of the phosphatase includes, for example, ERK 2 (*Biochem. Biophys. Res. Commun.*, 182: 14161422 (1992)), BTK (*Nature*, 361 (6409), 226-233 (1993)) and SYK (*J. Biol. Chem.*, 266: 15790-15796 (1991)), JAK 1 (*Molec. Cell. Biol.*, 2057-2065 (1991)), LAK 2 (*Biochem. Biophys. Res. Commun.*, 246: 627-633 (1998)), JAK 3 (*Proc. Natl. Acad. Sci.*, 91: 6374-6378 (1994)), ZAP 70 (*Cell*, 71: 649-662 (1992)), BLNK (*Immunity*, 9: 93-103 (1998)), FYN (*Proc. Natl. Acad. Sci. USA*, 83(15): 5459-5463 (1986)), LCK (*Biochim. Biophys. Acta*, 888(3): 286-295 (1986)) and the like, of which ERK 2 is more preferable.

The "antibody for a protein or polypeptide comprising an optional region in the extracellular region of the protein related to the present invention" may be any antibody such as a human antibody, a mouse antibody, a rat antibody, a domestic fowl antibody, a rabbit antibody or a goat antibody, as long as it inhibits binding of a ligand to the protein related to the present invention and does not have agonist activity for the protein related to the present invention. It may also be any one of their polyclonal or monoclonal antibodies, complete type or shortened type (e.g., F(ab')$_2$, Fab', Fab and Fv fragment and the like) antibodies, chimeric antibodies, humanized antibodies or complete human antibodies. Such antibodies can be produced by conventionally known antibody or antiserum production methods or in accordance with the methods described in Examples, wherein a protein or polypeptide comprising an optional region in the extracellular region of the protein related to the present invention is used as the antigen. The protein or polypeptide comprising an optional region in the extracellular region of the protein related to the present invention can be produced by conventionally known protein expression and purification methods or in accordance with the methods described in Examples.

The aforementioned substance which attenuates or inhibits suppression of intracellular signal transduction by the protein related to the present invention is useful as an agent for preventing and/or treating a cancer, an immunodeficiency disease or an infectious disease.

According to the specification of the present invention, the "agonist of a protein having an amino acid sequence identical to or substantially identical to an amino acid sequence selected from the amino acid sequences represented by SEQ ID NOs:1 to 6" means a substance which keeps or reinforces suppression of intracellular signal transduction by the protein related to the present invention. Such substance includes (i) a substance which cross-links the protein related to the present invention with a receptor expressed in a cell which expresses the protein;

(ii) an agonist antibody for the protein related to the present invention; and (iii) a ligand for the protein related to the present invention and the like.

In this connection, the "intracellular signal" includes, for example, intracellular signals generated from a B cell receptor or a B cell receptor complex, an activated Fc receptor, a CD14/TLR4 complex, an FcεRI and the like. Additionally, the "to keep or reinforce suppression of intracellular signal transduction by the protein related to the present invention" includes, for example, maintenance or increase of frequency of the dephosphorylated state of an intracellular signal transduction-carrying molecule by a phosphatase bound to the intracellular region of the protein related to the present invention and the like.

In this connection, the "receptor" in the "substance which cross-links the protein related to the present invention with a receptor expressed in a cell which expresses the protein" includes, for example, a B cell receptor or a B cell receptor complex, an activated Fc receptor, a CD14/TLR4 complex, an FcεRI and the like.

The "substance which cross-links the protein related to the present invention with a receptor expressed in a cell which expresses the protein" as the substance which keeps or reinforces suppression of intracellular signal transduction by the protein related to the present invention includes, for example, a protein, a polypeptide, an antibody and the like. The substance is preferably an antibody which recognizes both of the protein related to the present invention and a receptor expressed in a cell which expresses the protein.

The "agonist antibody for the protein related to the present invention" as the substance which keeps or reinforces suppression of intracellular signal transduction by the protein related to the present invention may be any antibody such as a human antibody, a mouse antibody, a rat antibody, a domestic fowl antibody, a rabbit antibody or a goat antibody, so long as it is an antibody which activates the protein related to the present invention, and it may also be any one of polyclonal or monoclonal antibodies, complete type or shortened type (e.g., F(ab')$_2$, Fab', Fab and Fv fragment and the like) antibodies, chimeric antibodies, humanized antibodies or complete human antibodies. Such antibodies can be produced by conventionally known antibody or antiserum production methods, or in accordance with the methods described in Examples wherein a protein or polypeptide comprising an optional region in the extracellular region of the protein related to the present invention is used as the antigen. The protein or polypeptide comprising an optional region in the extracellular region of the protein related to the present invention can be produced by conventionally known protein expression and purification methods.

The "ligand for the protein related to the present invention" as the substance which keeps or reinforces suppression of intracellular signal transduction by the protein related to the present invention is an intravital substance which binds to the extracellular region of the protein related to the present invention and has the activity to induce functions of the protein related to the present invention, and a polypeptide having its partial peptide is also included therein when such a substance is a protein.

As described the above, the substance which keeps or reinforces suppression of intracellular signal transduction by the protein related to the present invention is useful as an agent for preventing and/or treating an autoimmune disease, a rejection reaction after organ transplantation, an allergic disease or an inflammatory disease.

Screening Method of the Invention

According to the specification of the present invention, the method for screening an antagonist or agonist of the protein related to the present invention (sometimes referred to as screening method of the present invention hereinafter) can be carried out, for example, using a fluorescence polarization homogenous assay, a time-resolved fluorescence assay, a fluorescence resonance energy transfer assay, a chemical amplification type luminescence proximity homogenous assay, an RI assay, a bioluminescence resonance energy transfer assay, a two hybrid reporter gene assay, an intracellular $Ca^{2+}$ concentration measuring assay, an ELISA assay or the like.

The "protein or polypeptide comprising the extracellular region of the protein related to the present invention" in the method for screening an antagonist of the protein related to the present invention is a polypeptide comprising a region optionally selected from the region of amino acids 1 to 227 in the amino acid sequence represented by SEQ ID NO:1, a region optionally selected from the region of amino acids 1 to 227 in the amino acid sequence represented by SEQ ID NO:2, a region optionally selected from the region of amino acids 1 to 132 in the amino acid sequence represented by SEQ ID NO:3, a region optionally selected from the region of amino acids 1 to 137 in the amino acid sequence represented by SEQ ID NO:4, a region optionally selected from the region of amino acids 1 to 42 in the amino acid sequence represented by SEQ ID NO:5 or a region optionally selected from the region of amino acids 1 to 132 in the amino acid sequence represented by SEQ ID NO:6. In this connection, the "region being optionally selected" means a region which is necessary for keeping the activity of the protein related to the present invention to bind to a ligand.

The "protein or polypeptide comprising the intracellular region of the protein related to the present invention" is a protein or polypeptide which comprises the region of the aforementioned ITIM-like domain. In this connection, the tyrosine residue contained in the ITIM-like domain may be phosphorylated.

These polypeptides, those to which detection label such as an enzyme, a fluorescent material, a fluorescent protein, a luminescent material or a radioisotope or the like is added can be used. These detection labels may be added after or before the binding of a protein or polypeptide comprising the extracellular region of the protein related to the present invention to a ligand, via a substance or antibody capable of recognizing them. Specifically, the addition can be carried out by labeling a protein or polypeptide comprising the extracellular region of the protein related to the present invention or a ligand with biotin, and adding the aforementioned detection label labeled with avidin to the other one. This is the same also in the case of the binding of a protein or polypeptide comprising the intracellular region of the protein related to the present invention with a phosphatase.

The enzyme as the detection label, includes, for example, β-galactosidase, β-glucosidase, alkaline phosphatase, peroxidase, malate dehydrogenase and the like. The fluorescent material as the detection label, includes, for example, FITC (fluorescein isothiocyanate), PI (propidium iodide), Cy-Chrome, APC (allophycocyanine), R-PE (R-phycoerythrin), a fluorescent lanthanide chelate (e.g., europium, samarium, terbium, dysprosium or the like) and the like. The fluorescent protein as the detection label includes, for example, GFP (green fluorescent protein), AmCyan, ZsGreen, ZsYellow, AsRed, RCFP (reef coral fluorescent protein), DsRed, AcGFP1, HcRed1, CopGFP, PhiYFP-m. EYFP, KFP-Red and the like. The radioisotope as the detection label includes, for example, $[^{32}P]$, $[^{3}H]$, $[^{125}I]$, $[^{35}S]$ and $[^{14}C]$. The luminescent material as the detection label includes, for example, luminol, luminol derivatives, luciferin, lucigenin and the like.

In the description of the present invention, the "ligand" in the "step of allowing a protein or polypeptide comprising its extracellular region to contact with a ligand" of the screening method of the present invention is an intravital substance which binds to the extracellular region of the protein related to the present invention and has the activity to induce functions of the protein related to the present invention. A protein is preferred as such a ligand.

Examples of the "signal which is changed by the binding of the protein or polypeptide comprising its extracellular region of the protein related to the present invention with a ligand" or the "signal which is changed by the binding of the protein or polypeptide comprising its intracellular region of the protein related to the present invention with a phosphatase" includes a fluorescence generated by the aforementioned fluorescent material or fluorescent protein, a radiation from the radioisotope and the like as the detection labels. Additionally, development of a color by the reaction of the aforementioned enzyme as the detection label with a color developing substrate can also be exemplified. As the aforementioned enzyme, fluorescent material, fluorescent protein, luminescent material, radioisotope and color developing substrate, commercially available products can be used.

Although the "cell which expresses a protein having an amino acid sequence identical to or substantially identical to an amino acid sequence selected from the amino acid sequences represented by SEQ ID NOs:1 to 6" may be any cell which expresses the protein related to the present invention, it is preferably a cell transiently or steadily transformed by an expression vector capable of expressing the protein related to the present invention. As such an expression vector, a product which is generally put on the market can be used. Additionally, the cell to be transformed includes, for example, simian COS-1 cell, COS-7 cell, Chinese hamster CHO cell, human HEK 293T cell, U937 cell, Jurkat cell, HELA cell, Daudi cell, K562 cell, mouse L cell and the like.

Although the "cell which expresses a ligand" may be any cell which expresses the ligand, it is preferably a cell transiently or steadily transformed by an expression vector capable of expressing the ligand. As such an expression vector, a product which is generally put on the market can be used, and the aforementioned cell can be used as the cell to be transformed.

The "signal which is changed when a cell which expresses a protein having an amino acid sequence identical to or substantially identical to an amino acid sequence selected from the amino acid sequences represented by SEQ ID NOs:1 to 6 is allowed to contact with a cell that expresses a ligand or the ligand" includes, for example, signals (e.g., color development, fluorescence, luminescence, radiation and the like) corresponding to the intracellular cAMP concentration of such cell, intracellular $Ca^{2+}$ concentration, $IP_3$ concentration, phosphorylation or dephosphorylation of an intracellular signal transducer molecule (e.g., Erk 2 or the like), binding of a phosphatase to the protein related to the present invention, amount of a produced cytokine (e.g., interleukin 2 (IL-2) or the like) and the like.

As a screening method of the present invention, it can be carried out illustratively by the following method. Namely, an antibody for an activated receptor (e.g., BCR) which is co-expressed with the protein related to the present invention, an antibody for the protein related to the present invention or a ligand of the protein related to the present invention is simultaneously immobilized on a carrier such as agarose beads or a culture plate. When a cell expressing the protein related to the present invention (BRI 1-overexpressing cell, a B cell strain co-expressing BCR and BIR1, B cell, monocyte, peripheral mononuclear cell or the like) is added to the aforementioned immobilized carrier or plate to carry out the stimulation, a compound to be tested (a low molecular compound, a peptide, a solubilized protein, an antibody or the like) is added at the same time. After the culturing for a predetermined period of time, an antagonist of the protein related to the present invention can be screened, wherein the amount of interleukin 2 (IL-2) secreted into the culture supernatant, intracellular $Ca^{2+}$ concentration, phosphorylation of intracellular tyrosine residue of the protein related to the present invention, binding of a phosphatase to the protein related to the present invention and phosphorylation of an Erk 2 or the like intracellular signal transducer molecule are used as the index.

Additionally, a phosphorylated peptide comprising a region of the ITIM-like domain of the protein related to the present invention is biotinylated and allowed to bind to a carrier such as an agarose beads or a culture plate to which an anti-biotin antibody was immobilized, and a compound to be tested (e.g., a low molecular compound, a peptide, a solubilized protein, an antibody or the like) and a lysate of A20IIA1.6 cell are added thereto, followed by incubation for a predetermined period of time. After the reaction with a primary antibody for SHP-1, SHP-2, SHIP-1 or SHIP-2, amount of the phosphatase bound to the phosphorylated peptide is measured using a secondary antibody. A compound which reduces amount of the bound phosphatase can be screened as an antagonist of the protein related to the present invention.

A method for screening a compound which decreases or increases the expression level of the protein related to the present invention can be carried out, for example, by the following method. That is, cell (e.g., BIR1-overexpressing cells, human monocyte cell strain THP-1 cells, U 937 cells, CD 14-positive cells (monocytes) isolated from human peripheral blood, CD 19-positive cells (B cells) or the like) are inoculated onto a culture plate and cultured for a predetermined period of time together with a compound to be tested (e.g., a low molecular compound, a peptide, a solubilized protein, an antibody or the like), in the presence or absence of an inflammation stimulator (e.g., lipopolysaccharide (LPS), phorbol myristate acetate (PMA), interferon gamma (IFN-γ), INF-α or the like). RNA is extracted from the cells, and the expression level of the RNA is measured by quantitative RT-PCR using primers specific to the protein related to the present invention. Alternatively, an anti-human BIR1 monoclonal antibody is added to the cultured cells, then adding an FITC-labeled secondary antibody is added thereto to determine the BIR1 expressed on the cell surface by a flow cytometer. Furthermore, a cell lysate is prepared after the culturing, and the expression level of the protein is measured by Western blotting using an antibody for the protein related to the present invention.

Additionally, this can also be carried out by the following method. Specifically, an expression regulating region (e.g., promoter, enhancer, CAAT box, TATA box or the like), a DNA comprising 5'-non-translation region and a region around translation initiation region and a reporter gene (e.g., luciferase gene, chloramphenicol acetyltransferase (CAT) gene, β-galactosidase gene or the like) are connected with one another, and the thus prepared recombinant vector is transferred into appropriate cells. The cells are cultured in the presence or absence of a compound to be tested, under such an environment that transcription of the BIR1 gene can be effected to confirm transcription accelerating activity or transcription regulating activity of the compound to be tested by measuring the expression level of said reporter gene. The expression regulating region of BIR1 gene, 5'-non-translation region and a region around translation initiation region can be obtained by conventionally known methods.

Protein of the Invention

According to the specification of the present invention, the "protein having a substantially identical amino acid sequence" in the "protein having an amino acid sequence identical to or substantially identical to one amino acid sequence selected from the amino acid sequences represented by SEQ ID NOs:3 to 6, or a partial peptide thereof" also includes a protein having the same function of the protein having one amino acid sequence selected from the amino acid sequences represented by SEQ ID NOs:3 to 6, wherein several amino acids (preferably from 1 to 5 residues, more preferably 1 or 2 residues) in an amino acid sequence selected from SEQ ID NOs:3 to 6 are deleted, several amino acids (preferably from 1 to 5 residues, more preferably 1 or 2 residues) in the same are substituted with other amino acids, or several amino acids (preferably from 1 to 5 residues, more preferably 1 or 2 residues) are added to or inserted into the amino acid sequence, or which has an amino acid sequence of the combination thereof. In this case, the position of the aforementioned deletion, substitution or addition or insertion of amino acids is not particularly limited. Hereinafter, the "protein having an amino acid sequence identical to or substantially identical to one amino acid sequence selected from the amino acid sequences represented by SEQ ID NOs:3 to 6" may be called in some cases "the protein of the present invention".

Additionally, the protein of the present invention includes an amino acid sequence having a homology of about 70% or more, preferably about 80% or more, more preferably about 90% or more, particularly preferably about 95% or more, and most preferably about 98% or more with the amino acid sequence selected from SEQ ID NOs:3 to 6, over at least 20 residues or more, preferably 50 residues or more, more preferably 100 residues or more, and further preferably the entire region.

According to the protein in the specification of the present invention, the left terminal is the N-terminal (amino terminal) and the right terminal is the C-terminal (carboxyl terminal) in accordance with the conventional peptide marking.

The C-terminal of the protein of the present invention may be any one of a carboxyl group, carboxylate, amido and ester (—COOR). In this case, as R in the ester, for example, a C1-6 alkyl group (e.g., methyl, ethyl, n-propyl, isopropyl, n-butyl or the like), a C3-8 cycloalkyl group (e.g., cyclopentyl, cyclohexyl or the like), a C6-12 aryl group (e.g., phenyl, α-naphthyl or the like), a phenyl-C1-2 alkyl group (e.g., benzyl, phenetyl or the like), an α-naphthyl-C1-2 alkyl group (e.g., α-naphthylmethyl or the like), a C7-14 aralkyl group, pivaloyloxymethyl group and the like are used.

When the protein of the present invention has a carboxyl group at other than the C-terminal, those in which the carboxyl group is amidated or esterificated are also included in the protein of the present invention. Ester in the case includes the ester in the C-terminal and the like as mentioned above.

Additionally, the protein of the present invention also includes the protein those in which the amino group of an N-terminus amino acid residue (e.g., methionine residue or the like) is protected with a protecting group (e.g., a C1-6 acyl group (e.g., formyl group, acetyl group or the like) or the like), those in which an N-terminus glutamine residue formed by digestion in the living body is converted into pyroglutamic acid, those in which a substituent group (e.g., —OH, —SH, amino group, imidazole group, indole group, guanidino group or the like) on the side chain of an amino acid in the molecule is protected with an appropriate protecting group (e.g., a C1-6 acyl group (e.g., formyl group, acetyl group or the like) or the like), a conjugated protein such as a sugar chain-attached glycoprotein and the like.

The protein of the present invention is preferably a protein comprising the amino acid sequence represented by SEQ ID NO:3, a protein comprising the amino acid sequence represented by SEQ ID NO:4, a protein comprising the amino acid sequence represented by SEQ ID NO:5 or a protein comprising the amino acid sequence represented by SEQ ID NO:6, and more preferably a protein consisting of the amino acid sequence represented by SEQ ID NO:3, a protein consisting of the amino acid sequence represented by SEQ ID NO:4, a protein consisting of the amino acid sequence represented by SEQ ID NO:5 or a protein consisting of the amino acid sequence represented by SEQ ID NO:6.

According to the specification of the present invention, the "partial peptide" (sometimes referred to as partial peptide of the present invention hereinafter) in the "protein having an amino acid sequence identical to or substantially identical to an amino acid sequence selected from the amino acid sequences represented by SEQ ID NOs:3 to 6, or a partial peptide thereof" includes, for example, an optional region in the extracellular region of the protein of the present invention (e.g., a polypeptide comprising a region optionally selected from the region of amino acids 1 to 132 in the amino acid sequence represented by SEQ ID NO:3, a region optionally selected from the region of amino acids 1 to 137 in the amino acid sequence represented by SEQ ID NO:4, a region optionally selected from the region of amino acids 1 to 42 in the amino acid sequence represented by SEQ ID NO:5 or a region optionally selected from the region of amino acids 1 to 132 in the amino acid sequence represented by SEQ ID NO:6), and an optional region in the intracellular region of the protein of the present invention (e.g., a region optionally selected from the region of amino acids 156 to 248 in the amino acid sequence represented by SEQ ID NO:3, a region optionally selected from the region of amino acids 161 to 253 in the amino acid sequence represented by SEQ ID NO:4, a region optionally selected from the region of amino acids 66 to 158 in the amino acid sequence represented by SEQ ID NO:4 and a region optionally selected from the region of amino acids 156 to 176 in the amino acid sequence represented by SEQ ID NO:6) and the like. In this connection, the "region optionally selected" includes, for example, a region having an amino acid sequence of at least 10 or more, preferably 20 or more, more preferably 50 or more, most preferably 100 or more residues of the amino acid sequence of the present invention and the like.

Additionally, the partial peptide of the present invention also includes those in which several amino acids (preferably from 1 to 5 residues, more preferably 1 or 2 residues) in the amino acid sequence are deleted, those in which several amino acids (preferably from 1 to 5 residues, more preferably 1 or 2 residues) therein are substituted with other amino acids, or several amino acids (preferably from 1 to 5 residues, more preferably 1 or 2 residues) are added to or inserted into the amino acid sequence, or those which have an amino acid sequence in combination therewith. When the amino acid is deleted, substituted, added or inserted in the amino acid sequence like the aforementioned case, the position is not particularly limited.

The C-terminal of the partial peptide of the present invention may be any one of a carboxyl group, carboxylate, amido and ester (—COOR). In this connection, R of the ester includes similar groups described in the foregoing on the protein of the present invention. When the partial peptide of the present invention has a carboxyl group at other than the C-terminus, the partial peptide of the present invention also includes those in which the carboxyl group is amidated or esterificated. The ester in that case includes, for example, the aforementioned C-terminal ester and the like.

Similarly to the case of the aforementioned protein of the present invention, the partial peptide of the present invention also includes the peptide such as those in which the amino group of the N-terminus methionine residue is protected with a protecting group, those in which the Gln formed by digestion of the N-terminal side in the living body is converted into pyroglutamic acid, those in which a substituent group on the side chain of an amino acid in the molecule is protected with an appropriate protecting group, or a complex protein such as a sugar chain-linked glycoprotein.

The salt of the protein of the present invention or a partial peptide thereof includes, a physiologically acceptable salt with an acid or base. The acid addition salt includes, for example, a salt with an inorganic acid (e.g., hydrochloric acid, phosphoric acid, hydrobromic acid, sulfuric acid or the like) and a salt with an organic acid (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid or the like) and the like. The base addition salt includes, for example, a salt with ammonium hydroxide, an alkali or alkaline earth metal hydroxide (e.g., lithium hydroxide, sodium hydroxide, potassium hydroxide, calcium hydroxide, magnesium hydroxide or manganese hydroxide). The physiologically acceptable acid salt is especially preferred.

The partial peptide of the protein of the present invention is useful as an agent for preventing and/or treating, or diagnosing and/or testing a cancer, an immunodeficiency disease or an infectious disease, as a substance which inhibits binding of a ligand to the protein related to the present invention. Also, it can be used in the screening of an antagonist or agonist of the protein related to the present invention. Additionally, by using the protein of the present invention or a partial peptide thereof as the antigen, it can be also used for the preparation of an antibody for the protein of the present invention or a partial peptide thereof.

Polynucleotide of the Invention

According to the description of the present invention, the "polynucleotide encoding a protein having an amino acid sequence identical to or substantially identical to one amino acid sequence selected from the amino acid sequences represented by SEQ ID NOs:3 to 6, or a partial peptide thereof" may be any polynucleotide so long as it has a nucleotide sequence encoding the protein of the present invention or a partial peptide thereof. It is known that 1 to 6 codons encode one amino acid, for example, TTT or TTC corresponds to Phe; TTA, TTG, CTT, CTC, CTA or CTG corresponds to Leu; ATT, ATC or ATA corresponds to Ile; ATG corresponds to Met; GTT, GTC, GTA or GTG corresponds to Val; TCT, TCC, TCA or TCG corresponds to Ser; CCT, CCC, CCA or CCG corresponds to Pro; ACT, ACC, ACA or ACG corresponds to Thr; GCT, GCC, GCA or GCG corresponds to Ala; TAT or TAC corresponds to Tyr; CAT or CAC corresponds to His; CAA or CAG corresponds to Gln; AAT or AAC corresponds to Asn; AAA or AAG corresponds to Lys; GAT or GAC corresponds to Asp corresponds GAA or GAG corresponds to Glu; TGT or TGC corresponds to Cys; TGG corresponds to Trp; CGT, CGC, CGA or CGG corresponds to Arg; AGT or AGC corresponds to Ser; AGA or AGG corresponds to Arg; and GGT, GGC, GGA or GGG corresponds to Gly. Therefore, the polynucleotide coding for the protein of the present invention or a partial peptide thereof includes polynucleotides in which respective codons corresponding to respective amino acids are optionally combined. Hereinafter, the polynucleotide encoding a protein having an amino acid sequence identical to or substantially identical to one amino acid sequence selected from the amino acid sequences represented by SEQ ID NOs:3 to 6, or a partial peptide thereof, is sometimes referred to as "polynucleotide of the present invention".

The polynucleotide of the present invention may be any one of a genomic DNA, a cDNA, a synthetic DNA, an RNA and a DNA-RNA hybrid.

According to the specification of the present invention, in addition to the DNA having one nucleotide sequence selected from the nucleotide sequences represented by SEQ ID NOs:9 to 12, the polynucleotide of the present invention includes a polynucleotide having a nucleotide sequence which hybridizes with a complementary chain DNA of the DNA under a stringent condition and encoding a protein having substantially the same properties of the protein of the present invention. The hybridization can be carried out in accordance with the conventionally known methods (*Molecular Cloning* (Sambrook, J., Fritsch, E. F., Maniatis, T., Cold Spring Harbor Laboratory Press) (1989), *Gene,* 10: 63 (1980) and the like). The hybridization conditions can be determined by selecting temperature, ionic strength, primer length and the like appropriately. In general, the stringency is increased when the temperature is high and the ionic strength is law. The highly stringent conditions include, for example, hybridization at 65° C. in a buffer containing 0.5 M NaHPO$_4$, 7% SDS and 1 mM EDTA and washing treatment at 65° C. in a buffer containing 0.1×SSC and 0.1% SDS.

Such a polynucleotide includes, for example, a DNA comprising a nucleotide sequence having a homology of 90% or more, preferably 95% or more, more preferably 98% or more, with a DNA comprising one nucleotide sequence selected from the nucleotide sequences represented by SEQ ID NOs:9 to 12, over at least 20 bases, preferably 50 bases, more preferably 100 bases, further preferably the entire region, and the like.

Among the polynucleotides of the present invention, a polynucleotide encoding a protein having an amino acid sequence identical to or substantially identical to the amino acid sequences represented by SEQ ID NO:3, or a partial peptide thereof, is preferably a DNA comprising the nucleotide sequence represented by SEQ ID NO:9 or comprising its partial sequence, more preferably a DNA comprising the nucleotide sequence represented by SEQ ID NO:9, further preferably a DNA consisting of the nucleotide sequence represented by SEQ ID NO:9.

Among the polynucleotides of the present invention, a polynucleotide encoding a protein having an amino acid sequence identical to or substantially identical to the amino acid sequences represented by SEQ ID NO:4, or a partial peptide thereof, is preferably a DNA comprising the nucleotide sequence represented by SEQ ID NO:10 or comprising its partial sequence, more preferably a DNA comprising the nucleotide sequence represented by SEQ ID NO:10, further preferably a DNA consisting of the nucleotide sequence represented by SEQ ID NO:10.

Among the polynucleotides of the present invention, preferred a polynucleotide encoding a protein having an amino acid sequence identical to or substantially identical to the amino acid sequences represented by SEQ ID NO:5, or a partial peptide thereof, is preferably a DNA comprising the nucleotide sequence represented by SEQ ID NO:11 or comprising its partial sequence, more preferably a DNA comprising the nucleotide sequence represented by SEQ ID NO:11, further preferably a DNA consisting of the nucleotide sequence represented by SEQ ID NO:11.

Among the polynucleotides of the present invention, a polynucleotide encoding a protein having an amino acid sequence identical to or substantially identical to the amino acid sequences represented by SEQ ID NO:6, or a partial peptide thereof, is preferably a DNA comprising the nucleotide sequence represented by SEQ ID NO:12 or comprising its partial sequence, more preferably a DNA comprising the nucleotide sequence represented by SEQ ID NO:12, further preferably a DNA consisting of the nucleotide sequence represented by SEQ ID NO:12.

The polynucleotide of the present invention can be used as a template for producing the protein of the present invention or a partial peptide thereof.

The polynucleotide of the present invention can also be used in the screening of the present invention.

The polynucleotide of the present invention can be used for preparing a transgenic animal, a knockout animal or an animal with reduced expression of the protein of the present invention or a protein related to the present invention, in accordance with conventionally known methods.

Since a polynucleotide comprising a nucleotide sequence complementary to the polynucleotide of the present invention or a part thereof can detect mRNA of the protein of the present invention, for example, when used as a primer or a probe, it can be used as a primer or probe for diagnosing and/or testing an immunodeficiency disease, a cancer or an infectious disease or an autoimmune disease, a rejection reaction after organ transplantation, an allergic disease or an inflammatory disease. Such a primer or probe can be labeled with an enzyme, a fluorescent material, a luminescent material or a radioisotope in accordance with conventional methods.

The polynucleotide of the present invention or a polynucleotide comprising a nucleotide sequence complementary to the polynucleotide of the present invention or a part thereof can be used for a gene therapy for preventing and/or treating a cancer, an immunodeficiency disease or an infectious disease or an autoimmune disease, a rejection reaction after organ transplantation, an allergic disease or an inflammatory disease, by introduction into cells in the living body.

The polynucleotide comprising a nucleotide sequence complementary to the polynucleotide of the present invention or a part thereof includes so-called antisense DNA, siRNA (small interfering RNA), ribozyme and the like.

The antisense DNA for the polynucleotide of the present invention can be produced by inserting a part of the polynucleotide of the present invention (preferably DNA) into the antisense region of the aforementioned vector.

The siRNA for the polynucleotide of the present invention is a double-stranded RNA which comprises a part of the RNA encoding the protein of the present invention and an RNA complementary thereto. The siRNA can be produced by designing it based on the sequence of the polynucleotide of the present invention, in accordance with the conventionally known method (*Nature,* 411: 494-498 (2001)).

The ribozyme can be produced by designing it based on the sequence of the polynucleotide of the present invention, in accordance with the conventionally known method (*TRENDS in Molecular Medicine,* 7: 221 (2001)). For example, it can be produced by connecting a conventionally known ribozyme to a part of RNA encoding the protein of the present invention. The part of RNA encoding the protein of the present invention includes, for example, a part adjacent to a region which can be digested by a conventionally known ribozyme (an RNA fragment). Since such an antisense DNA, siRNA or ribozyme can lower level of the protein of the present invention in cells, it is useful as an agent for preventing and/or treating a cancer, an immunodeficiency disease or an infectious disease.

When the polynucleotide of the present invention or a polynucleotide comprising a nucleotide sequence complementary to the polynucleotide of the present invention or a part thereof is used as an agent for preventing and/or treating a cancer, an immunodeficiency disease or an infectious disease or an autoimmune disease, a rejection reaction after organ transplantation, an allergic disease or an inflammatory disease, the polypeptide alone, or after inserting it into an appropriate vector such as a retrovirus vector or adenovirus vector, it can be administered to human or a mammal in accordance with the usual way. Such a polynucleotide can be used directly or after making it into a pharmaceutical preparation together with a carrier such as an auxiliary substance for accelerating its introduction into cells (e.g., liposome, HVJ liposome or the like).

According to the specification of the present invention, when nucleotides, amino acids and the like are shown by abbreviations, they are based on the conventional abbreviations used in the field, and their examples include DNA (deoxyribonucleic acid), cDNA (complementary deoxyribonucleic acid), RNA (ribonucleic acid), A (adenine), T (thymine), G (guanine), C (cytosine), Gly (glycine), Ala (alanine), Val (valine), Leu (leucine), Ile (isoleucine), Ser (serine), Thr (threonine), Cys (cysteine), Met (methionine), Glu (glutamic acid), Asp (aspartic acid), Lys (lysine), Arg (arginine), His (histidine), Phe (phenylalanine), Tyr (tyrosine), Trp (tryptophan), Pro (proline), Asn (asparagine), Gln (glutamine) and the like. Additionally, when there is a possibility of existing optical isomers regarding amino acids, they show L-form unless otherwise noted.

Antibody for the Protein of the Invention

According to the specification of the present invention, the antibody for a protein having an amino acid sequence identical to or substantially identical to an amino acid sequence selected from the amino acid sequences represented by SEQ ID NOs:3 to 6 or for a partial peptide thereof (sometimes referred to as antibody of the present invention hereinafter) may be any antibody of a human antibody, a mouse antibody, a rat antibody, a domestic fowl antibody, a rabbit antibody and a goat antibody, so long as it is an antibody which recognizes the protein of the present invention or a partial peptide thereof, and it may also be any one of their polyclonal or monoclonal antibodies, complete type or shortened type (e.g., $F(ab')_2$, Fab', Fab and Fv fragment and the like) antibodies, chimeric antibodies, humanized antibodies or complete human antibodies. Such antibodies can be produced in accordance with the conventionally known antibody or antiserum production methods, using a partial peptide of the extracellular region of the protein of the present invention as the antigen. A partial peptide of the extracellular region of the protein can be produced in accordance with the conventionally known protein expression and purification methods.

The antibody of the present invention are preferably monoclonal antibodies, more preferably shortened type antibodies, chimeric antibodies, humanized antibodies and complete human antibodies of monoclonal antibodies, and further preferably are complete human antibodies of monoclonal antibodies.

Since the antibody for the protein of the present invention or a partial peptide thereof can detect the protein of the present invention, it can be used as an agent for diagnosing and/or testing an immunodeficiency disease, a cancer or an infectious disease or an autoimmune disease, a rejection reaction after organ transplantation, an allergic disease or an inflammatory disease.

Production Method and Purification Method of Protein or Polypeptide

A protein or polypeptide comprising an optional region in the extracellular region of the protein related to the present invention, which can be cited as an antagonist of the protein, a protein or polypeptide comprising the extracellular region of the protein related to the present invention or a protein or polypeptide comprising the intracellular region of the same, which can be used in the screening method of the present invention, and the protein of the present invention or a partial peptide thereon can be produced by conventionally known protein expression methods and purification methods or by the methods described in Examples. For example, (1) a method for purifying and isolating them from the living body or cultured cells;

(2) a method for synthesizing peptides; and (3) a method for producing them with the use of genetic recombination techniques; and the like can be cited.

The method described in (3) is industrially desirable, and as general techniques for that, the standard techniques described for example in *Molecular Cloning* (Sambrook, J., Fritsch, E. F., Maniatis, T., Cold Spring Harbor Laboratory Press) (1989) and *Current Protocols in Molecular Biology* (Ausubel, F. M., John Wiley & Sons, Inc. (1989)) can be used.

An expression system (host-vector system) for producing a protein or peptide with the use of genetic recombination techniques includes expression systems of bacteria, yeast, insect cells and mammalian cells.

For example, when it is expressed in *Escherichia coli*, an expression vector is prepared by adding an initiation codon (ATG) to the 5'-terminal of a DNA coding for encoding a mature protein part; connecting the thus obtained cDNA to the downstream of an appropriate promoter (e.g., trp promoter, lac promoter, XPL promoter, T7 promoter or the like); and inserting it into a vector which is able to function in *E. coli* cells (e.g., pBR322, pUC18, pUC19 or the like). Next, an *E. coli* strain (e.g., *E. coli* DH 1, *E. coli* JM 109, *E. coli* HB 101 strain or the like) transformed with the expression vector is cultured in an appropriate medium to obtain the objective protein or peptide from the resulting cells. Alternatively, when a bacterial signal peptide (e.g., a signal peptide of pelB or the like) is used, the objective protein or peptide of interest can be secreted into the periplasmic space. Additionally, a fusion protein with other polypeptide can also be produced.

Also, when it is expressed in yeast, an expression vector is prepared by connecting a DNA encoding the protein of the present invention or a partial peptide thereof to the downstream of an appropriate promoter (e.g., PHO5 promoter, PGK promoter, GAP promoter, ADH promoter or the like), and inserting it into a vector capable of functioning in yeast (e.g., pSH19, pSH15 or the like). Next, a yeast strain transformed with this expression vector (e.g., *Saccharomyces cerevisiae* AH 22, AH 22R⁻ or 20B-12, *Shizosaccharomyces pombe* NCYC 1913, *Pichia pastoris* KM 71 or the like) is cultured in an appropriate medium to obtain the objective protein or peptide.

Also, when it is expressed in an insect cell, an expression vector is prepared by connecting a DNA encoding the protein of the present invention or a partial peptide thereof to the downstream of an appropriate promoter (e.g., polyhedrin promoter, P10 promoter or the like), and inserting it into a virus vector which is able to function in insect cells. As the insect cells, for example, when the virus is AcNPV, a *Barathra* larva-derived established cell line (Sf cell) or the like is used. When the virus is BmNPV, a silkworm-derived established cell line (BmN cell) or the like is used. As the Sf cell, for example, Sf9 cell (ATCC CRL 1711) or Sf21 cell (In Vivo, 13: 213-217 (1977)) is used. As the insect, larvae of silkworm and the like are used. When an insect cell or insect is transformed, for example, it can be carried out in accordance with the method described in *Bio/Technology*, 6: 47-55 (1988).

Also, when it is expressed in a mammalian cell, an expression vector is prepared by inserting a DNA encoding the protein of the present invention or a partial peptide thereof into the downstream of an appropriate promoter (e.g., SV40 promoter, LTR promoter, metallothionein promoter or the like) in an appropriate vector (e.g., a retrovirus vector, a Papillomavirus vector, a vaccinia virus vector, an SV40 system vector or the like). Next, an appropriate mammalian cell (e.g., human HEK 293T cell, monkey COS-1 cell, COS-7 cell, Chinese hamster CHO cell, mouse L cell, NSO cell or the like) is transformed with the thus obtained expression vector, and the resulting transformant is cultured using an appropriate medium to express the protein of the present invention or a partial peptide thereof. Additionally, a fusion protein can also be produced by ligation with a cDNA fragment encoding other polypeptide such as an antibody constant region (Fc moiety).

Additionally, as a method for producing a protein or peptide making use of genetic recombination techniques, a cell-free synthesis system (Sambrook J., *Molecular Cloning* 2nd ed. (1989)) can also be used.

The peptide synthesis method may be either a solid phase synthesis method or a liquid phase synthesis method. The objective protein can be produced by condensing partial peptides or amino acids which can constitute the protein of the present invention with the remaining parts and eliminating the protecting group when the product has a protecting group. In the case, the condensation and elimination of protecting group are carried out in accordance with the methods described in, for example, (i) M. Bodanszky, M. A. Ondetti, *Peptide Synthesis*, Interscience Publishers, New York (1966),
(ii) Schroeder, Luebke, *The Peptide*, Academic Press, New York (1965),
(iii) Nobuo Izumiya et al., *The foundation and Experiments of Peptide Synthesis* (written in Japanese), Maruzen Co., Ltd. (1975),
(iv) Naoaki Yajima and Shunpei Sakakibara, *Biochemical Experimentation Course* 1, Chemistry of Protein IV (written in Japanese), 205, (1977), and
(v) edited by Naoaki Yajima, *Development of Medical Supplies—a Second Series*, Volume 14, Peptide Synthesis (written in Japanese), Hirokawa Shoten.

The protein or a partial peptide thereof obtained by the above manner can be isolated and purified by general biochemical methods such as salting out, ion exchange chromatography, hydrophobic chromatography, affinity chromatography, reverse phase chromatography, adsorption chromatography, chromatofocusing, isoelectric precipitation, gel filtration, and ultrafiltration.

Additionally, it is also possible to express the protein of the present invention or a partial peptide thereof as a fusion protein with other protein or a tag (an antibody constant region, glutathione S-transferase, protein A, FLAG tag, hexahistidine tag or the like). Since the fusion protein can be purified by affinity chromatography and/or digestion with an appropriate protease (e.g., enterokinase, thrombin or the like), there is an advantage as it can be efficiently purified.

Method for Preparing or Producing Polynucleotide

A polynucleotide encoding the protein related to the present invention and a polynucleotide encoding the protein of the present invention or a partial peptide thereof can be obtained or produced by conventionally known preparation or production methods and purification methods, or by the methods described in Examples. For example, it can be obtained by chemical synthesis, or by amplifying it by PCR method using a synthetic DNA primer encoding the protein of the present invention or a partial peptide thereof, or by a hybridization method which uses a synthetic DNA encoding the protein of the present invention or a partial peptide thereof as the probe.

The human tissue or cell to be used for obtaining a polynucleotide encoding the protein of the present invention or a partial peptide thereof by the PCR method or hybridization method includes spleen, lymph node, bone marrow, leukocyte, monocyte, B cell and the like. By separating mRNA from the aforementioned tissue or cell, a cDNA library is prepared by standard genetic recombination techniques. The objective cDNA can be obtained by screening the library using a specific probe synthesized based on one nucleotide sequence selected from the nucleotide sequences represented by SEQ ID NOs:7 to 12. Alternatively, the objective cDNA can be amplified by synthesizing sense and antisense primers for amplifying the objective nucleotide sequence, which is based on a nucleotide sequence selected from the nucleotide sequences represented by SEQ ID NOs:7 to 12, and carrying out PCR using the cDNA library as the template. It is desirable to carry out the PCR using an automatic thermal cycler. The reaction can be completed in the presence of a thermostable polymerase (e.g., Taq or the like), a template DNA and primers, by carrying out from about 25 to 40 cycles, wherein 1 cycle includes denaturation of DNA (e.g., 98° C., 10 to 30 seconds), annealing of primers (e.g., 56° C., 30 seconds to 1 minute) and elongation reaction in the presence of 4 kinds of substrates (dNTP) (e.g., 72° C., 30 seconds to 10 minutes), and subsequently carrying out heating at 70 to 75° C. for 5 to 15 minutes. Additionally, cDNA libraries of various human tissues are commercially available recently, and when they are used, the reaction can be carried out in accordance with the method described in the instructions attached thereto. The hybridization method can be carried out in accordance with the method described, for example, in *Molecular Cloning* (Sambrook, J., Fritsch, E. F., Maniatis, T., Cold Spring Harbor Laboratory Press) (1989) or *Gene,* 10: 63 (1980). A necessary amount of the DNA can be obtained by introducing a vector DNA comprising the DNA into an appropriate host and allowing it to proliferative.

Method for Preparing or Producing Antibody

Although the antibody for a protein or polypeptide comprising an optional region in the extracellular region of the protein related to the present invention or the antibody for the protein of the present invention or a partial peptide thereof may be either a polyclonal antibody or a monoclonal antibody, as long as it is an antibody which can recognize each of the protein or polypeptide comprising an optional region in the extracellular region of the protein related to the present invention and the protein of the present invention or a partial peptide thereof, a monoclonal antibody derived from a mammal is particularly desirable. The monoclonal antibody derived from a mammal includes those which are produced by a hybridoma and those which are produced by a host transformed with an expression vector comprising an antibody gene prepared by a genetic engineering technique.

An antigen-producing hybridoma can be prepared in the following manner with use of conventionally known techniques. Namely, a protein or polypeptide comprising an optional region in the extracellular region of the protein related to the present invention, a partial peptide of the protein of the present invention or a cell expressing the protein related to the present invention or the protein of the present invention (e.g., a forced expression cell or the like) is used as a sensitized antigen, which is used in the immunization in accordance with a general immunization method. The thus obtained immune cells are fused with a conventionally known parent cell by a general cell fusion method, and a monoclonal antibody producer cell is cloned by a general screening method. Although the mammal to be immunized with the sensitized antigen is not particularly limited, it is desirable to select it by taking its compatibility with the parent cell to be used in the cell fusion (myeloma cell) into consideration, and an animal of rodents, such as, mouse, rat and hamster, is generally used. Immunization of the animal with a sensitized antigen is carried out in accordance with a conventionally known method. As the myeloma cell to be fused with the aforementioned immunized cell, various conventionally known cell strains can be used. Cell fusion of the immunized cell with myeloma cell can be carried out in accordance with a conventionally known method such as the method of Milstein et al. (*Methods Enzymol.*, 73: 3-46 (1981)). The thus obtained fused cells are selected by culturing them in a general selection medium such as HAT medium (a culture liquid containing hypoxanthine, aminopterin and thymidine). The culturing with this HAT medium is continued for generally from several days to several weeks until other cells than the hybridomas (un-fused cells) die out. Next, screening and cloning of a hybridoma producing an antibody which binds to the protein of the present invention is carried out by the general limiting dilution method. The antibody can be obtained by purifying culture supernatant of the hybridoma obtained in this manner. The purification can be carried out by optionally combining general biochemical methods such as salting out, ion exchange chromatography and affinity chromatography.

A polyclonal antibody can be produced by a general method in which a mammal (e.g., rabbit, goat, sheep or the like) is immunized using a protein or polypeptide comprising an optional region in the extracellular region of the protein related to the present invention or the protein of the present invention or a partial peptide thereof as the sensitization antigen, and antiserum is recovered and purified. The purification can be carried out by optionally combining general biochemical methods such as salting out, ion exchange chromatography and affinity chromatography.

Additionally, the antibody can also be obtained using genetic engineering techniques. Namely, mRNA is prepared from splenocyte or lymphocyte of an animal immunized by using a protein or polypeptide comprising an optional region in the extracellular region of the protein related to the present invention, a partial peptide of the protein of the present invention or a cell which expresses the protein related to the present invention or the protein of the present invention (e.g., over-expressing cell), as the sensitization antigen, or from a monoclonal antibody producer hybridoma, and a cDNA library is prepared using this mRNA as the template. A clone producing an antibody which reacts with the sensitization antigen is screened and the thus obtained clone is cultured. The objective antibody can be purified from the resulting culture supernatant by optionally combining general biochemical methods such as salting out, ion exchange chromatography, affinity chromatography and the like. When the antibody is used as a medicine, a humanized antibody or human antibody having low immunogenicity is desirable. The humanized antibody can be prepared by genetic engineering techniques using hypervariable region of the aforementioned monoclonal antibody (*Method in Enzymology*, 203: 99-121 (199)). The human antibody can be prepared by immunizing a mouse whose immune system is replaced by its human counterpart (*Nat. Genet.*, 15: 146-156 (1997)).

An antibody for a protein or polypeptide comprising an optional region in the extracellular region of the protein related to the present invention, as an antagonist for the protein related to the present invention, can be selected by the following method. Namely, an antibody for an activated receptor (e.g., BCR or the like) which is co-expressed with the protein related to the present invention, or a ligand of the protein related to the present invention is simultaneously immobilized on a carrier such as agarose beads or a culture plate. When a cell expressing the protein related to the present invention (e.g., B cell, monocyte, over-expressing cell or the like) is added to the aforementioned immobilized carrier or plate to carry out stimulation, an antibody to be tested is added at the same time. Whether or not it attenuates or inhibits suppression of intracellular signal transduction by the protein related to the present invention is evaluated, using intracellular $Ca^{2+}$ concentration, phosphorylation of intracellular tyrosine residue of the protein related to the present invention, binding of a phosphatase to the protein related to the present invention, phosphorylation of a signal transducer molecule such as an Erk2, or produced amount of a cytokine (e.g., IL-2 or the like), as the index.

An agonist antibody for the protein related to the present invention can be selected by the following method. That is, an antibody to be tested is simultaneously immobilized on a carrier such as agarose beads or a culture plate. By adding a cell expressing the protein of the present invention (e.g., B cell, monocyte, over-expressing cell or the like) to the aforementioned immobilized carrier or plate, whether or not it keeps or reinforces suppression of intracellular signal transduction by the protein related to the present invention is evaluated, using intracellular $Ca^{2+}$ concentration, phosphorylation of intracellular tyrosine residue of the protein of the present invention, binding of a phosphatase to the protein related to the present invention, phosphorylation of a signal transducer molecule such as an Erk2, or produced amount of a cytokine (e.g., IL-2 or the like), as the index.

Application to Medical Supplies

Since an antagonist of the protein related to the present invention or a pharmaceutical composition comprising the same has an immunopotentiation activity, it can be used for preventing and/or treating of cancers, immunodeficiency diseases or infectious diseases.

Examples of the cancers or tumors, wherein its prevention and/or treatment can be expected by the administration of an antagonist of the protein related to the present invention or a pharmaceutical composition comprising the same, include lingual cancer, gingival cancer, malignant lymphoma, malignant melanoma (melanoma), maxillary cancer, nasal cancer, nasal cavity cancer, laryngeal cancer, pharyngeal cancer, glioma, myeloma, glioma, neuroblastoma, papillary carcinoma of thyroid, follicular carcinoma of thyroid, medullary carcinoma of thyroid, primary pulmonary carcinoma, squamous cell carcinoma, adenocarcinoma, alveolar carcinoma, large cell undifferentiated carcinoma, small cell undifferentiated carcinoma, carcinoid, testicular tumor, prostatic cancer, breast cancer (e.g., papillary adenocarcinoma, comedocarcinoma, mucous tumor, medullary carcinoma, lobular carcinoma, scirrhous carcinosarcoma, metastatic tumor), mammary Paget disease, mammary sarcoma, bone tumor, thyroid gland cancer, gastric cancer, liver cancer, acute myelocytic leukemia, acute promyelocytic leukemia, acute myelomonocytic leukemia, acute monocytic leukemia, acute lymphocytic leukemia, acute undifferentiated leukemia, chronic myeloid leukemia, chronic lymphocytic leukemia, adult T cell leukemia, malignant lymphoma (e.g., lymphosarcoma, reticulum cell sarcoma, Hodgkin disease or the like), multiple myeloma, primary macroglobulinemia, infantile leukemia, esophageal carcinoma, gastric cancer, gastrocolic leiomyosarcoma, gastrointestinal malignant lymphoma, pancreas-gall bladder cancer, duodenal cancer, large bowel cancer, primary cancer of liver (e.g., hepatocellular carcinoma, bile duct cancer or the like), hepatoblastoma, uterine intraepithelial carcinoma, cervical squamous cell carcinoma, adenocarcinoma of uterus, adenosquamous carcinoma of uterus, uterine body adenocarcinoma, uterine carcinosarcoma, invasive hydatidiform mole of uterus, malignant chorioepithelioma of uterus, uterine malignant melanoma, ovarian cancer, mesodermal mixed tumor, renal carcinoma, renal pelvic transitional cell carcinoma, ureteral transitional cell carcinoma, papillary carcinoma of urinary bladder, bladder transitional cell carcinoma, urethral squamous cell carcinoma, urethral adenocarcinoma, Wilms tumor, rhabdomyosarcoma, fibrosarcoma, osteosarcoma, chondrosarcoma, synovial sarcoma, myxosarcoma, liposarcoma, Ewing sarcoma, skin squamous cell carcinoma, skin basal cell carcinoma, skin Bowen disease, skin Paget disease, skin malignant melanoma, malignant mesothelioma, metastatic adenocarcinoma, metastatic squamous cell carcinoma, metastatic sarcoma, mesothelioma (e.g., pleural mesothelioma, peritoneal mesothelioma, pericardial mesothelioma or the like) and the like.

Examples of the immunodeficiency diseases, wherein its prevention and/or treatment can be expected by the administration of an antagonist of the protein related to the present invention or a pharmaceutical composition comprising the same, include acquired immunodeficiency syndrome (AIDS) caused by human immunodeficiency virus infection (e.g., *candida* esophagitis, *carinii* pneumonia, toxoplasmosis, tuberculosis, *Mycobacterium avium* complex infection, cryptosporidiosis, *Cryptococcus* meningitis, cytomegalic inclusion disease, opportunistic infection such as progressive multifocal leuco-encephalopathy, or the like), immunodeficiency and primary immunodeficiency syndrome accompanied by a serious disease (e.g., cancer, hypoplastic anemia, leukemia, myelofibrosis, renal insufficiency, diabetes, hepatic disease or splenic disease) and the like.

It is considered that a virus uses a coupling suppression factor of immune cells as a method for escaping from immunoprophylaxis of infected host (*Journal of Experimental Medicine*, 191, 11: 1987-1997 (2000)). Since viral infection is partly caused by such an escaping function of viruses, it is considered that immune reaction of immune cells with viruses can be improved by the administration of an antagonist of the protein related to the present invention or a pharmaceutical composition comprising the same.

Examples of the infectious diseases, wherein its prevention and/or treatment can be expected by the administration of an antagonist of the protein related to the present invention or a pharmaceutical composition comprising the same, include infections with human hepatitis viruses (e.g., hepatitis B, hepatitis C, hepatitis A and hepatitis E), human retrovirus, human immunodeficiency viruses (e.g., HIV 1 and HIV 2), human T cell leukemia virus or human T lympho-tropic virus (e.g., HTLV 1 and HTLV 2), type 1 or type 2 herpes simplex virus, Epstein-Barr virus, cytomegalovirus, varicella-shingles virus, human herpes viruses (e.g., human herpes virus 6 and the like), polio virus, measles virus, rubella virus, Japanese encephalitis virus, mumps virus, influenza virus, common cold viruses (e.g., adenovirus, enterovirus, rhinovirus and the like), a virus which causes serious acute respiratory organ syndrome (SARS), Ebola virus, Western Nile virus and the like.

Additionally, it is considered that this is also effective for infections with pathogenic protozoans (e.g., *Trypanosoma*, malaria parasite and *Toxoplasma*), bacteria (e.g., *Mycobacterium, Salmonella* and *Listeria*), fungi (e.g., *Candida*) and the like.

Since the agonist of the protein related to the present invention has immunosuppressive activity, it can be used for preventing and/or treating of a disease selected from auto- immune diseases, rejection reaction after organ transplantation, allergic diseases and inflammatory diseases.

Examples of the autoimmune disease, wherein its prevention and/or treatment can be expected by the administration of an agonist of the protein related to the present invention or a pharmaceutical composition comprising the same, include arthritis, autoimmune hepatitis, autoimmune glomerulonephritis, autoimmune insulitis, autoimmune orchitis, autoimmune oophoritis, ulcerative colitis, Sjogren's syndrome, Crohn disease, Behcet disease, Wegner granulomatosis, hypersensitivity angiitis, periarteritis nodosa, Hashimoto disease, myxoedema, Basedow disease, Addison disease, autoimmune hemolytic anemia, sudden thrombopenia, pernicious anemia, myasthenia gravis, demyelinating disease, aortitis syndrome, psoriasis, pemphigus, pemphigoid, collagen disease (e.g., systemic lupus erythematosus, rheumatoid arthritis, diffuse scleroderma, systemic progressive sclerosis, dermatomyositis, polyarteritis nodosa, rheumatic fever or the like), Guillain-Barre syndrome, polyglandular autoimmune syndrome type II, primary biliary cirrhosis, vitiligo vulgaris, type I diabetes mellitus, and the like. Additionally, a disease having high value of lupus anticoagulation factor can be also cited. In this connection, the disease having high value of lupus anticoagulation factor includes, systemic lupus erythematosus, arterial thrombosis (e.g., cerebral infarction or the like), venous thrombosis, habitual abortion, thrombopenia, anti-phospholipid antibody syndrome and the like can be exemplified.

Examples of the rejection reaction after organ transplantation, wherein its prevention and/or treatment can be expected by the administration of an agonist of the protein related to the present invention or a pharmaceutical composition comprising the same, include rejection reaction after renal transplantation, liver transplantation, heart transplantation and/or lung transplantation, rejection reaction by bone marrow transplantation, graft versus host disease and the like.

Examples of the allergic disease, wherein its prevention and/or treatment can be expected by the administration of an agonist of the protein related to the present invention or a pharmaceutical composition comprising the same, include asthma, bronchial asthma, atopic dermatitis, nettle rash, allergic rhinitis (e.g., pollinosis or the like), allergic conjunctivitis (e.g., pollinosis or the like), allergic enterogastritis, anaphylactic shock, food allergy and the like.

Examples of the inflammatory disease, wherein its prevention and/or treatment can be expected by the administration of an agonist of the protein related to the present invention or a pharmaceutical composition comprising the same, include dermatitis (e.g., contact dermatitis, atopic dermatitis and the like), colitis (e.g., ulcerative colitis, Crohn disease and the like), angiitis (e.g., Takayasu arteritis, giant cell arteritis (temporal arteritis), polyarteritis nodosa, Wegener granuromatosis, Churg-Strauss syndrome (allergic granuromatous angiitis), allergic skin angiitis, Henoch-Schonlein purpura, hypersensitivity angiitis, angiitis syndrome, thromboangiitis obliterans (Buerger disease), nodular vasculitis and the like), arthritis (e.g., chronic rheumatoid arthritis, rheumatoid arthritis, osteoarthritis, tuberculous arthritis, suppurative arthritis, psoriatic arthritis, internal derangement of knee joint, idiopathic osteonecrosis, osteoarthritis and the like), hepatitis (e.g., viral hepatitis, autoimmune hepatitis and the like), nephritis (e.g., acute nephritis, chronic glomerulonephritis, rapidly progressive nephritic syndrome, acute glomerulonephritis after hemolytic streptococcal infection, membranoproliferative glomerulonephritis, Goodpasture syndrome, mesangial proliferative glomerulonephritis (IgA nephropathy), interstitial nephritis and the like), gastritis (e.g., acute infectious gastritis, allergic gastritis, chronic gastritis and the like), pancreatitis, enteritis, laryngitis, neuritis and the like.

An antagonist or agonist of the protein related to the present invention may be administered as an agent for concomitant use by combining with other agent for
(1) compensating and/or reinforcing the preventive and/or therapeutic effect of the preventive and/or therapeutic agent of the present invention,
(2) improving disposition and absorption, and reducing its dose of the preventive and/or therapeutic agent of the present invention and/or
(3) reducing side effects of the preventive agent or therapeutic agent of the present invention.

The agent for concomitant use of antagonist or agonist of the protein related to the present invention with other agent may be administered in the form of a combination agent prepared by formulating both of the components in one pharmaceutical preparation or may take a form for its administering as separate pharmaceutical preparations. When administered as separate pharmaceutical preparations, simultaneous administration and administration at different times are included therein. Additionally, the administration at different times may be effected by firstly administering the antagonist or agonist of the protein related to the present invention and then administering other agent, or the other agent may be firstly administered, followed by the administration of the antagonist or agonist of the protein related to the present invention. Respective administration method may be the same or different from each other.

The aforementioned other agent may be a low molecular compound, or may be a high molecular protein, polypeptide, polynucleotide (DNA, RNA or gene), antisense, decoy or antibody, a vaccine or the like. Dose of the other agent can be optionally selected using the clinically used dose as the standard. Also, blending ratio of the antagonist or agonist of the protein related to the present invention with the other agent can be optionally selected based on the age and body weight of the subject to be administered, administration method, administration time, disease or symptom to be treated or a combination thereof. For example, from 0.01 to 100 parts by mass of the other agent may be used based on 1 part by weight of the antagonist or agonist of the protein related to the present invention. The other agent may be administered in combination of optional two or more species at an optional ratio. Additionally, based on the aforementioned mechanism, not only those which have been so far found but also those which will be found in the future are also included in the other agent that compensates and/or reinforces the preventive and/or therapeutic effect of the antagonist or agonist of the protein related to the present invention.

The disease which is prevented and/or treated by the aforementioned agent for concomitant use is not particularly limited, and it may be any disease in which the preventive and/or therapeutic effect of the antagonist or agonist of the protein related to the present invention can be compensated and/or reinforced.

In the chemotherapy and radiotherapy for cancers, a side effect of severely reducing proliferation of lymphocytes is unavoidable. Administration of the antagonist of the protein related to the present invention or a pharmaceutical composition comprising the same shows the effect to stimulate or proliferate the reduced lymphocytes and can also suppress the severe side effects accompanied by the general chemotherapy to the minimum. Also, the same thing can be said on the radiotherapy. Additionally, the dose of a chemotherapeutic agent or irradiated amount of radiation can be reduced from the generally used dose or amount of radiation, by concomitant use with the antagonist of the protein related to the present invention or a pharmaceutical composition comprising the same.

The antagonist of the protein related to the present invention can be used concomitantly with a conventional chemotherapeutic agent or made into a combination agent therewith. As such a chemotherapeutic agent, for example, an alkylating agent, a nitrosourea agent, a metabolic antagonist, a carcinostatic antibiotic, a plant-derived alkaloid, a topoisomerase inhibitor, a hormone therapy agent, a hormone antagonist, an aromatase inhibitor, a P glycoprotein inhibitor, a platinum complex derivative, other immunotherapy agents and other antitumor agents. Additionally, it can also be used concomitantly, or made into a combination agent, with a leuko(neutro)penia treating agent, a thrombopenia treating agent, an antiemetic agent or a cancer pain treating agent, as a cancer treatment auxiliary agent.

The antagonist of the protein related to the present invention can be used concomitantly, or made into a combination agent, with other immunopotentiation substance. Such an immunopotentiation substance includes, for example, various cytokines, tumor antigens and the like. The cytokine which stimulates immune reaction includes, GM-CSF, M-CSF, G-CSF, interferon-α, β or γ, IL-1, IL-2, IL-3, IL-12 and the like. Additionally, a B7 ligand derivative, a CD3 antibody, a CD28 antibody and a CTLA-4 antibody can also increase the immune reaction.

Administration of a cancer antigen can also improve specific immune reaction of an immunocyte for a cancer cell, and can give additional or synergistic reinforcement by its concomitant use with the antagonist of the protein related to the present invention. The cancer antigen can be prepared as a purified protein when its gene is clear, or as a lysate of the cancer cell itself when unclear. Such a cancer antigen includes, for example, malignant melanoma MAGE-1 and MAGE-3-derived HLA-A1 and HLA-A2 commitment peptides, MART-1 and gp100. Additionally, HER2/neu peptide of breast cancer and ovarian cancer and MUC-1 peptide of adenocarcinoma, along with NY-ESO-1 of metastatic cancer, can be also cited.

The antagonist of the protein related to the present invention can be used concomitantly, or made into a combination agent, with an antiviral agent, an antibiotic preparation, an antibacterial agent or a visceral mycosis treating agent.

The antiviral agent includes, for example, an anti-HIV agent, an anti-influenza virus agent, an anti-herpes virus agent, interferon-α or β, and various species of immunoglobulin.

The antagonist of the protein related to the present invention can be used concomitantly, or made into a combination agent, with a vaccine of a virus or pathogen. The vaccine includes for example, poliomyelitis vaccine, measles virus vaccine, Japanese encephalitis vaccine, BCG vaccine, triple vaccine, mumps vaccine, varicella vaccine, influenza vaccine, hepatitis A vaccine, hepatitis B vaccine and cholera vaccine. In this connection, the anti-HIV agent includes, for example, a reverse transcriptase inhibitor (e.g., AZT, ddI, 3TC, d4T or the like), a protease inhibitor (e.g., saquinavir mesylate, ritonavir, nelfinavir mesylate, amprenavir, delavirdine mesylate, saquinavir, lopinavir/ritonavir or the like) or a CCR5 receptor antagonist. The anti-influenza virus agent includes, for example, influenza vaccine, oseltamivir phosphate, zanamivir hydrate, amantadine hydrochloride and the like.

The other agent for compensating and/or reinforcing the preventive and/or therapeutic effect of the agonist of the protein related to the present invention for an autoimmune disease, a rejection reaction after organ transplantation, an allergic disease or an inflammatory disease includes, for example, a steroid agent, a non-steroidal anti-inflammatory agent, an immunosuppressive agent, an anti-allergic agent (e.g., a chemical transmitter release inhibitor, an antihistaminic, a thromboxane synthase inhibitor, a thromboxane antagonist, a Th2 cytokine inhibitor or the like), a phosphodiesterase inhibitor (PDE4), a mediator release inhibitor and the like.

External preparations among the steroid agents includes, for example, clobetasol propionate, diflorasone acetate, fluocinonide, mometasone furan carboxylate, betamethasone dipropionate, betamethasone butyrate propionate, betamethasone valerate, difluprednate, budesonide, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, predonisolone valerate acetate, fluocinolone acetonide, beclometasone dipropionate, triamcinolone acetonide, flumetasone pivalate, alclometasone propionate, clobetasone butytrate, prednisolone, peclometasone propionate, fludroxycortide and the like.

Internal preparations or injections among the steroid agents includes, for example, cortisone acetate, hydrocortisone, hydrocortisone sodium phosphate, hydrocortisone sodium succinate, fludrocortisone acetate, prednisolone, prednisolone acetate, prednisolone sodium succinate, prednisolone butyl acetate, prednisolone sodium phosphate, halopredone acetate, methylprednisolone, prednisolone acetate, prednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, bethamethasone and the like, and as inhalations includes, for example, bethamethasone propionate, fluticasone propionate, budesonide, flunisolide, triamcinolone, ST-126P, ciclesonide, dexamethasone paromitionate, mometasone furancarbonate, prasterone sulfonate, deflazacort, methylprednisolone suleptanate, methylprednisolone sodium succinate and the like.

The non-steroidal anti-inflammatory agent includes, for example, aspirin, loxonin, diclofenac, celecoxib, tiaprofenic acid, alminoprofen, flurbiprofen axetil, zaltoprofen, suprofen, ketoprofen, pranoprofen, fentiazac, droxicum, ibuprofen, aceclofenac, amfenac sodium, tenoxicam, oxaprozin, piroxicam, emorfazone, tolfenamic acid, indometacin farnesil, proglumetacin maleate, sulindac, mofezolac, etodolac, lonazolac calcium, ampiroxicam, mesalazine, deflazacort, nimesulide, etoricoxib, ketorolac, trometamol, palecoxib, lobenzarit disodium, auranofin, loxoprofen sodium, bucillamine, actarit, piroxicam cinnamate, nabumetone, salazosulfapyridine, lormoxicam, meloxicam, diacerein, rofecoxib, valdecoxib and the like.

The basic non-steroidal anti-inflammatory agent includes, for example, tiaramide hydrochloride, tinoridine hydrochloride, epirizole, emorfazone and the like.

The immunosuppressive agent includes, for example, azathioprine, ascomycin, everolimus, orthoclone OKT3, corticosteroid, salazosulfapyridine, ciclosporin, cyclophosphamide, sirolimus, tacrolimus hydrate, deoxyspergualin, bucillamine, prednisolone, mycophenolate mofetil, mizoribine, methylprednisolone, methotrexate, leflunomide, anti-human lymphocyte globulin and the like.

The chemical transmitter release inhibitor among anti-allergic agents includes, for example, sodium cromoglycate, tranilast, amlexanox, repirinast, ibudilast, pemirolast potassium, dazanolast, nedocromil, cromoglycate, israpafant and the like.

The antihistaminic among anti-allergic agents includes, for example, diphenhydramine, diphenylpyraline hydrochloride, diphenylpyraline teoclate, clemastine fumarate, dimenhydrinate, dl-chlorpheniramine maleate, d-chlorpheniramine maleate, triprolidine hydrochloride, promethazine hydrochloride, alimemazine tartarate, isothipendyl hydrochloride, homochlorcyclizine hydrochloride, hydroxyzine, cyproheptadine, levocabastine hydrochloride, astemizole, hepotastine, desloratadine, TAK-427, ZCR-2060, NIP-530, mometasone furoate, mizolastine, BP-294, andolast, auranofin, acrivastine and the like.

The thromboxane synthase inhibitor among anti-allergic agents includes, for example, ozagrel hydrochloride, imitrodust sodium and the like. The thromboxane antagonist includes, for example, ceratrodust, lamatroban, domitroban calcium hydrate, KT-2-962 and the like. The Th2 cytokine inhibitor includes, for example, suplatotost tosilate, sonatimod, T-614, SR-31747 and the like.

The phosphodiesterase inhibitor (PDE4) includes, for example, cilomilast, roflumilast, alophyrin, atizolam, cipamfilin, rolipram, OPC-6535, ONO-6126, IC-485, AWD-12-281, CC-10004, CC-1088, KW-4490, lirimilast, ZK-117137, YM-976, BY-61-9987, CC-7085, CDC-998, MEM-1414, ND-1251, Bay 19-8004, D-4396, PD-168787, NIK-616, SCH-351591, V-1294A and the like.

The mediator release inhibitor includes, for example, amlexanox, ibudilast, sodium cromoglycate, dazanolast, tranilast, pemirolast potassium, repirinast and the like.

When active component of the antagonist or agonist of the protein related to the present invention is used as a medicine, it can be administered alone or as a pharmaceutical composition by mixing it with various pharmacologically acceptable preparation auxiliaries. In general, it is administered according to each purpose, in the form of a pharmaceutical preparation suited for its use such as oral administration, intravenous administration, topical administration or percutaneous administration.

Dose of such a component varies depending on the age, body weight, symptom, therapeutic effect, administration method, treating time and the like. In general, it is orally administered within the range of from 1 ng to 10000 mg, per adult per once, from once in several days, once in 3 days, once in 2 days, once a day to several times, or parenterally administered (preferably intravenous administration) within the range of from 1 ng to 1000 mg, per adult per once, from once in several days, once in 3 days, once in 2 days, once a day to several times, or continuously administered into a vein within the range of from 1 hour to 24 hours a day.

As a matter of course, since the dose changes by various conditions as described in the foregoing, there is a case in which an amount smaller than the aforementioned dose is sufficient or a case in which its administration of exceeding the range is necessary.

When a concomitant preparation of the antagonist or agonist of the protein related to the present invention with other agent is administered, it is used as solid preparations for internal use or solutions for internal use for use in its oral administration, or as injections, external preparations, suppositories, eye drops, inhalations or the like for use in its parenteral administration.

The solid preparations for internal use for use in the oral administration includes tablets, pills, capsules, powders, granules and the like. Hard capsules and soft capsules are included in the capsules. Also, the tablets include sublingual tablets, buccal patch tablets, buccal quick disintegrating tablets and the like.

In such solid preparation for internal use, one or two or more of active substances are used as such or after making into a pharmaceutical preparation in accordance with the usual way by mixing them with an excipient (e.g., lactose, mannitol, glucose, microcrystalline cellulose, starch or the like), a binder (e.g., hydroxypropyl cellulose, polyvinyl pyrrolidone, aluminum magnesium metasilicate or the like), a disintegrator (e.g., calcium cellulose glycolate or the like), a lubricant (e.g., magnesium stearate or the like), a stabilizer, a solubilizing agent (e.g., glutamic acid, aspartic acid or the like) or the like. Additionally, these may be coated with a coating agent (e.g., sucrose, gelatin, hydroxypropylcellulose, hydroxypropylmethyl-cellulose phthalate or the like) or coated with two or more layers, if necessary. Further, capsules of the absorbable substance such gelatin is also included therein.

Sublingual tablets are produced in accordance with a conventionally known method. For example, these are used after making one or two or more of active substances into a pharmaceutical preparation in accordance with the usual way by mixing them with an excipient (e.g., lactose, mannitol, glucose, microcrystalline cellulose, colloidal silica, starch or the like), a binder (e.g., hydroxypropyl cellulose, polyvinyl pyrrolidone, aluminum magnesium metasilicate or the like), a disintegrator (e.g., starch, L-hydroxypropylcellulose, carboxymethylcellulose, croscarmellose sodium, calcium cellulose glycolate or the like), a lubricant (e.g., magnesium stearate or the like), a swelling agent (e.g., hydroxypropylcellulose, hydroxypropylmethylcellulose, carbopol, carboxymethylcellulose, polyvinyl alcohol, xanthan gum, guar gum or the like), a swelling auxiliary (e.g., glucose, fructose, mannitol, xylitol, erythritol, maltose, trehalose, a phosphate, a citrate, a silicate, glycine, glutamic acid, arginine or the like), a stabilizer, a solubilizing agent (e.g., polyethylene glycol, propylene glycol, glutamic acid, aspartic acid or the like), a flavor (e.g., orange, strawberry, mint, lemon, vanilla or the like) or the like. Also, these may be coated with a coating agent (e.g., sucrose, gelatin, hydroxypropylcellulose, hydroxypropylmethylcellulose phthalate or the like) or coated with two or more layers, if necessary. Additionally, generally used additive agents such as an antiseptic, an antioxidant, a coloring agent, a sweetener and the like can also be added thereto, if necessary. Buccal patch tablets are prepared in accordance with a conventionally known method. For example, these are used after making one or two or more of active substances into a pharmaceutical preparation in accordance with the usual way by mixing them with an excipient (e.g., lactose, mannitol, glucose, microcrystalline cellulose, colloidal silica, starch or the like), a binder (e.g., hydroxypropyl-cellulose, polyvinyl pyrrolidone, aluminum magnesium metasilicate or the like), a disintegrator (e.g., starch, L-hydroxypropyl-cellulose, carboxymethylcellulose, croscarmellose sodium, calcium cellulose glycolate or the like), a lubricant (e.g., magnesium stearate or the like), an adhesive agent (e.g., hydroxypropylcellulose, hydroxypropylmethylcellulose, carbopol, carboxymethylcellulose, polyvinyl alcohol, xanthan gum, guar gum or the like), an adhesion auxiliary (e.g., glucose, fructose, mannitol, xylitol, erythritol, maltose, trehalose, a phosphate, a citrate, a silicate, glycine, glutamic acid, arginine or the like), a stabilizer, a solubilizing agent (e.g., polyethylene glycol, propylene glycol, glutamic acid, aspartic acid or the like), a flavor (e.g., orange, strawberry, mint, lemon, vanilla or the like) and the like. Also, these may be coated with a coating agent (e.g., sucrose, gelatin, hydroxypropylcellulose, hydroxypropylmethylcellulose phthalate or the like) or coated with two or more layers, if necessary. Additionally, generally used additive agents such as an antiseptic, an antioxidant, a coloring agent, a sweetener and the like can also be added thereto, if necessary. Buccal quick disintegrating tablets are prepared in accordance with a conventionally known method. For example, one or more of active substances are used as such or after making them into a pharmaceutical preparation in accordance with the usual way by mixing the active substances, prepared in advance by coating the bulk or granulated bulk particles with an appropriate coating agent (e.g., ethyl cellulose, hydroxypropylcellulose, hydroxypropylmethylcellulose, an acrylic acid methacrylic acid copolymer or the like) and a plasticizer (e.g., polyethylene glycol, triethyl citrate or the like), with an excipient (e.g., lactose, mannitol, glucose, microcrystalline cellulose, colloidal silica, starch or the like), a binder (e.g., hydroxypropyl-cellulose, polyvinyl pyrrolidone, aluminum magnesium metasilicate or the like), a disintegrator (e.g., starch, L-hydroxypropylcellulose, carboxymethylcellulose, croscarmellose sodium, calcium cellulose glycolate or the like), a lubricant (e.g., magnesium stearate or the like), a dispersion auxiliary (e.g., glucose, fructose, mannitol, xylitol, erythritol, maltose, trehalose, a phosphate, a citrate, a silicate, glycine, glutamic acid, arginine or the like), a stabilizer, a solubilizing agent (e.g., polyethylene glycol, propylene glycol, glutamic acid, aspartic acid or the like), a flavor (e.g., orange, strawberry, mint, lemon, vanilla or the like) or the like. Also, these may be coated with a coating agent (e.g., sucrose, gelatin, hydroxypropyl-cellulose, hydroxypropylmethylcellulose phthalate or the like) or coated with two or more layers, if necessary. Additionally, generally used additive agents such as an antiseptic, an antioxidant, a coloring agent, a sweetener and the like can also be added thereto, if necessary.

The internal solutions for the oral administration include pharmaceutically acceptable waters, suspensions, emulsions, syrups, elixirs and the like. In such solutions, one or two or more of active substances are dissolved, suspended or emulsified in a generally used diluent (e.g., purified water, ethanol, a mixed liquid thereof or the like). Additionally, this solutions may contain wetting agents, suspending agents, emulsifying agents, sweeteners, flavors, aromatics, preservatives, buffer agents or the like.

For example, the external preparations for the parenteral administration include ointments, gels, creams, fomentations, patches, liniments, aerosols, inhalations, sprays, aerosols, eye drops, nasal drops and the like. These contain one or two or more of active substances and are prepared by a conventionally known method or a generally used prescription.

Ointments are produced by a conventionally known or generally used method. For example, they are prepared by mixing or melting one or two or more of active substances in a base. The ointment base is selected from those which are conventionally known or generally used. For example, those which are selected from a higher fatty acid or higher fatty acid ester (e.g., adipic acid, myristic acid, palmitic acid, stearic acid, oleic acid, adipic acid ester, myristic acid ester, palmitic acid ester, stearic acid ester, oleic acid ester or the like), waxes (e.g., yellow beeswax, spermaceti wax, ceresin or the like), a surfactant (e.g., polyoxyethylene alkyl ether phosphoric acid ester or the like), a higher alcohol (e.g., cetanol, stearyl alcohol, cetostearyl alcohol or the like), a silicon oil (e.g., dimethylpolysiloxane or the like), hydrocarbons (e.g., hydrophilic petrolatum, white petrolatum, purified lanolin, liquid paraffin or the like), glycols (e.g., ethylene glycol, diethylene glycol, propylene glycol, polyethylene glycol, macrogol or the like), a plant oil (e.g., castor oil, olive oil, sesame oil, turpentine oil or the like), an animal oil (e.g., mink oil, yolk oil, squalane, squalene or the like), water, an absorption accelerator and a rash preventing agent are used alone or as a mixture of two or more. Additionally, they may contain moisture keeping agents, preservatives, stabilizers, antioxidants, flavors or the like.

Gels are produced by a conventionally known or generally used method. For example, they are prepared by melting one or two or more of active substances in a base. The gel base is selected from those which are conventionally known or generally used. For example, those which are selected from a lower alcohol (e.g., ethanol, isopropyl alcohol or the like), a gelling agent (e.g., carboxymethyl cellulose, hydroxyethyl cellulose, hydroxypropyl cellulose, ethyl cellulose or the like), a neutralizing agent (e.g., triethanolamine, diisopropanolamine or the like), a surfactant (e.g., polyethylene glycol monostearate or the like), gums, water, an absorption accelerator and a rash preventing agent are used alone or as a mixture of two or more. Additionally, they may contain preservatives, antioxidants, flavors or the like.

Creams are produced by a conventionally known or generally used method. For example, they are prepared by melting or emulsifying one or two or more of active substances in a base. The cream base is selected from those which are conventionally known or generally used. For example, those which are selected from a higher fatty acid ester, a lower alcohol, hydrocarbons, a polyhydric alcohol (e.g., propylene glycol, 1,3-butylene glycol or the like), a higher alcohol (e.g., 2-hexyldecanol, cetanol or the like), an emulsifying agent (e.g., polyoxyethylene alkyl ethers, fatty acid esters or the like), water, an absorption accelerator and a rash preventing agent are used alone or as a mixture of two or more. Additionally, they may contain preservatives, antioxidants, flavors or the like.

Fomentations are produced by a conventionally known or generally used method. For example, they are produced by melting one or two or more of active substances in a base, and spreading and coating it on a support as a kneaded material. The fomentation base is selected from those which are conventionally known or generally used. For example, those which are selected from a thickener (e.g., polyacrylic acid, polyvinyl pyrrolidone, acacia, starch, gelatin, methyl cellulose or the like), a wetting agent (e.g., urea, glycerol, propylene glycol or the like), a bulking agent (e.g., kaolin, zinc oxide, talc, calcium, magnesium or the like), water, a solubilizing agent, a tackifier and a rash preventing agent are used alone or as a mixture of two or more. Additionally, they may contain preservatives, antioxidants, flavors or the like.

Patches are produced by a conventionally known or generally used method. For example, they are prepared by melting one or two or more of active substances in a base, and spreading and coating it on a support. The patch base is selected from those which are conventionally known or generally used. For example, those which are selecting from a high molecular base, a fat, a higher fatty acid, a tackifier and a rash preventing agent are used alone or as a mixture of two or more. Additionally, preservatives, antioxidants, flavors or the like may also be contained therein.

Liniments are produced by a conventionally known or generally used method. For example, they are prepared by dissolving, suspending or emulsifying one or two or more of active substances in one or two or more of materials selected from water, an alcohol (e.g., ethanol, polyethylene glycol or the like), a higher fatty acid, glycerol, soap, an emulsifying agent and a suspending agent. Additionally, they may contain preservatives, antioxidants, flavors or the like.

The aerosols, inhalations and sprays may contain a stabilizer such as sodium hydrogen sulfite and a buffer agent which provides tonicity, which is a tonicity agent such as sodium chloride, sodium citrate or citric acid, in addition to the generally used diluent. Production methods of sprays are described in detail, for example, in U.S. Pat. Nos. 2,868,691 and 3,095,355.

The injections for parenteral administration include all injections and also include drip infusions. For example, they include intramuscular injections, subcutaneous injections, intradermal injections, intraarterial injections, intravenous injections, intraperitoneal injections, spinal injections, intravenous drip infusions and the like.

The injections for parenteral administration include solutions, suspensions, emulsions and solid injections which are used by dissolving or suspending in a solvent when used. The injections are used by dissolving, suspending or emulsifying one or two or more of active substances in a solvent. As the solvent, for example, distilled water for injection, physiological saline, plant oil, alcohols such as propylene glycol, polyethylene glycol or ethanol, and the like and a combination therewith are used. Additionally, such injections may contain a stabilizing agent, a solubilizing agent (e.g., glutamic acid, aspartic acid, Polysorbate 80 (registered trademark) or the like), a suspending agent, an emulsifying agent, a soothing agent, a buffer agent, a preservative or the like. These are sterilized in the final process or prepared by an aseptic operation. Alternatively, it is possible to produce an aseptic solid preparation such as a freeze-dried product, and to use it by dissolving in sterilized or aseptic distilled water for injection or other solvent prior to its use.

The eye drops for parenteral administration include ophthalmic solutions, suspension type ophthalmic solutions, emulsion type ophthalmic solutions, ophthalmic solutions of a dissolving type when used and eye ointments.

These eye drops are produced in accordance with conventionally known methods. For example, these are used by dissolving, suspending or emulsifying one or two or more of active substances in a solvent. As the solvent of eye drops, for example, aseptic purified water, physiological saline, other aqueous solvent or non-aqueous solvent for injection (e.g., a plant oil or the like) and the like and a combination thereof are used. The eye drops may contain tonicity agents (e.g., sodium chloride, concentrated glycerol and the like), buffer agents (e.g., sodium phosphate or sodium acetate and the like), surfactants (e.g., Polysorbate 80 (registered trademark), Polyoxyl 40 stearate, for example, polyoxyethylene hydrogenated castor oil and the like), stabilizers (e.g., sodium citrate or sodium edetate and the like), antiseptics (e.g., benzalkonium chloride or paraben and the like), by optionally selecting them, if necessary. These are sterilized in the final process or prepared by an aseptic operation. Alternatively, it is possible to produce an aseptic solid preparation such as a freeze-dried product, and to use it by dissolving in sterilized or aseptic sterilized purified water or other solvent prior to its use.

The inhalations for parenteral administration include aerosols, powders for inhalation or solutions for inhalation, and the solutions for inhalation may be such a form that they are used by dissolving or suspending in water or other appropriate solvent at the time of their use.

These inhalations are produced in accordance with conventionally known methods.

For example, in the case of solutions for inhalation, they are prepared by optionally selecting antiseptics (e.g., benzalkonium chloride or paraben and the like), coloring agents, buffer agents (e.g., sodium phosphate or sodium acetate and the like), tonicity agents (e.g., sodium chloride or concentrated glycerol and the like), thickeners (e.g., carboxy vinyl polymer and the like), absorption promoters and the like, if necessary.

In the case of powders for inhalation, they are prepared by optionally selecting lubricants (e.g., stearic acid and salts thereof and the like), binders (e.g., starch, dextrin and the like), excipients (e.g., lactose or cellulose and the like), coloring agents, antiseptics (e.g., benzalkonium chloride or paraben and the like), absorption accelerating agents and the like, if necessary.

When the solutions for inhalation are administered, a sprayer (e.g., an atomizer or nebulizer) is generally used, and an inhaler for powder agents is generally used when the powders for inhalation are administered.

Other compositions for parenteral administration include suppositories for rectal administration, pessaries for vaginal administration and the like, which comprise one or two or more active substances and are prescribed in the usual way.

EXAMPLES

The present invention is described below in more detail with reference to examples, but the present invention is not limited thereto.

Example 1: Expression Profile of Human BIR1

In order to examine expression of BIR1 mRNA in human normal tissues, blood cells and cell strains, BIR1-specific primers were designed, and PCR was carried out using TaKaRa Ex Taq (manufactured by TaKaRa). Sequences of the primers used therein are shown below.

```
                                             (SEQ ID NO: 13)
5'-GAACAGGCTCCTCTTCTGGAG-3'

(SEQ ID NO: 14)
5'-GGTTCACCTTTTCCATCCTGG-3'
```

The PCR was carried out by firstly keeping at 96° C. for 1 minute, subsequently repeating 35 cycles of a temperature operation of 98° C. for 10 seconds, 56° C. for 30 seconds and 72° C. for 30 seconds, and finally keeping at 72° C. for 10 minutes.

Human MTC Panel I, Human MTC Panel II, Human Immune System MTC Panel and Human Blood Fractions MTC Panel (manufactured by BD Clontech) were used in the expression analysis of human normal tissues and blood cells, and cDNA prepared from total RNA by reverse transcription reaction in accordance with the usual way was used in the expression analysis of human cell lines. Each of the PCR products was subjected to agarose gel electrophoresis, and then the gel was stained with ethidium bromide to obtain image data by BioDoc-It System (manufactured by UVP). The results are shown in FIG. 1.

BIR1 was expressed at high level in immune system tissues such as spleen and lymph node and in CD14-positive cells (monocytes) and CD19-positive cells (B cells). Additionally, in the case of human cell lines, expression of BIR1 was found in K562 and HL-60 which have the monocyte differentiation ability, monocyte system cell strains U937 and THP-1, and B cell strains Raji, CCRF-SB and FLEB-14-14.

Example 2: Expression of Human BIR1 by Various Inflammation Stimuli

Expression of BIR1 by various inflammation stimuli was examined using human monocyte system cell strains. At a density of $1 \times 10^6$ cells/2 mL, each of THP-1 cells and U937 cells were stimulated with lipopolysaccharide (LPS) (1 μg/mL), phorbol myristate acetate (PMA) (100 ng/mL), IFN-γ (100 ng/mL), TNF-α (10 ng/mL) or LPS+IFN-γ (1 μg/mL+100 ng/mL), for 1, 3, 8, 24, 48 or 120 hours, and the total RNA was recovered. Amount of RNA of BIR1 was determined by ABI PRISM 7000 Sequence Detection System (manufactured by Applied Biosystems) using BIR1-specific primers; 5'-CACAGCCATGGAAGTTGGAATC-3' (SEQ ID NO:15) and 5'-GAGTGTTTGGCCTCATCTTGG-3' (SEQ ID NO:16) and QuantiTect SYBR Green RT-PCR Kit (manufactured by QIAGEN). The PCR was carried out by firstly keeping at 50° C. for 30 minutes and then at 95° C. for 15 minutes. Next, a temperature operation of 94° C. for 10 seconds, 56° C. for 30 seconds and 72° C. for 1 minute was repeated 45 times. As a result, as shown in FIG. 2, gene expression of BIR1 was increased in 8 to 48 hours after the stimulation other than TNF-α in THP-1 cells, and was increased in 24 to 48 hours after any of the stimuli in U937 cells.

Example 3: Expression of BIR1 in Autoimmune Disease Patient-Derived Blood Cells

Expression of BIR1 in autoimmune disease patient-derived various blood cells were detected using Autoimmune Disease Profiling Array (manufactured by BD Clontech). A BIR1-specific probe labeled with [α-$^{32}$P] dCTP (manufactured by Perkin Elmer) was prepared using Random Primer DNA Labeling Kit Ver. 2 (manufactured by TaKaRa), using a human BIR1 partial length cDNA fragment as the template. The partial length cDNA fragment used therein is shown in SEQ ID NO:17.

The pre-hybridization, hybridization and washing operations after the probe preparation were carried out in accordance with the instructions attached thereto. By obtaining image data using BAS 2000 (manufactured by FUJIFILM), PSL (photo-stimulated luminescence; proportional to radiation dose) value of each dot was calculated from the image data using the Image Analyzer II of BAStation Ver. 2.21, and the expressed amount of BIR1 in each sample was numerically expressed. As the statistical analysis, Wilcoxon (Mann-Whitney) test was carried out on healthy persons. The results are shown in FIG. 3.

In comparison with healthy persons, expression of BIR1 was significantly increased in monocytes of lupus anticoagulation factor patients and B cells of the patients of articular rheumatism, multiple sclerosis and Takayasu arteritis.

Example 4: Identification of Human BIR1 Splicing Variants

PCR was carried out using human CD14-positive cell (monocyte)- and CD19-positive cell (B cell)-derived cDNA (Human Blood Fractions MTC Panel) (manufactured by BD Clontech) as the template and using TaKaRa LA Taq (manufactured by TaKaRa). The designed primers specific to human BIR1 are shown below.

5'-ATGTGGAGCCATTTGAACAGGCTCCTC-3' (SEQ ID NO: 18)

5'-TCAGAAGTTGAGTTCAGAATAGAC-3' (SEQ ID NO: 19)

The PCR was carried out by firstly keeping at 96° C. for 1 minute, subsequently repeating 35 cycles of a temperature operation of 98° C. for 10 seconds, 56° C. for 30 seconds and 72° C. for 1 minute and 30 seconds, and finally keeping at 72° C. for 10 minutes. The PCR products were subjected to agarose gel electrophoresis and then isolated and subcloned into T/A vector. In accordance with the instructions attached to BigDye Terminator v3.1 Cycle Sequencing Kit (manufactured by Applied Biosystems), the sequence of each cDNA fragment was determined by ABI PRISM 3100 Genetic Analyzer (manufactured by Applied Biosystems).

As a result, in addition to the known isoform (two immunoglobulin (Ig) domains are present; BIR1L) (SEQ ID NOs:1 and 2), an isoform in which the Ig domain at the C-terminal side is deleted (BIR1S1) (SEQ ID NO:3), an isoform in which the Ig domain at the N-terminal side is deleted (BIR1S2) (SEQ ID NO:4), an isoform in which both of the Ig domains are deleted (BIR1ΔIg) (SEQ ID NO:5) and an isoform in which a part of the intracellular region of BIR1S1 is deleted (BIR1ΔCyt) (SEQ ID NO:6) were newly identified. The Ig domain at the N-terminal side is a part which corresponds to the amino acid numbers 41 to 122 of the amino acid sequence described in SEQ ID NO:1, and the Ig domain at the C-terminal side is a part which corresponds to the amino acid numbers 138 to 203 of the amino acid sequence represented by SEQ ID NO:1.

Example 5: Preparation of Cell Stably Expressing Mouse FcγRIIB-Human BIR1 Chimeric Protein Examination was carried out whether or not BIR1 transmits an inhibitory signal. The following materials were prepared in accordance with the methods reported in *Proc. Natl. Acad. Sci. U.S.A.*, 98: 13866-13871 (2001), *J. Immunol.*, 162: 3168-3175 (1999) and the like. An FcR chimeric protein expression vector was constructed by inserting a DNA encoding an FcR-hBIR1 (wt) chimeric protein (SEQ ID NO:20), which was prepared by connecting the intracellular region of BIR1 (amino acid numbers 251 to 343 of SEQ ID NO:1) to the C-terminal side of the extracellular region, transmembrane region and 6 intracellular region amino acids (amino acid numbers 1 to 252) of mouse FcγRIIB (FcR), into downstream of the β-actin promoter. Also, an expression vector of a mutant (FcR-hBIR1 (YWF)) (SEQ ID NO:21), in which all of the 6 tyrosine residues of the intracellular region of BIR1 were replaced by phenylalanine residues, was prepared using QuickChange Multi Site-Directed Mutagenesis Kit (manufactured by Stratagene). These FcR chimeric protein expression vectors and an expression vector for an FcR chimeric protein of a known inhibitory receptor human KIR2DL3 (FcR-hKIR2DL3) (SEQ ID NO:22) were introduced into a mouse B cell strain A20IIA1.6 (a mouse FcγRIIB-deficient cell strain) (*J. Immunol.*, 136: 348-356 (1986)) using Gene Pulser Xcell Electroporation System (manufactured by BIO-Rad). Each of the introduced cells was stained with an FITC-labeled rat anti-mouse CD16/CD32 antibody (2.4G2) (manufactured by BD Pharmingen), and then expression level of the FcR chimeric protein was examined by FACSCalibur (manufactured by BD Biosciences).

As shown in FIG. 4, these were cells which stably express the FcR chimeric protein at almost the same level.

Example 6: Inhibition of Intracellular $Ca^{2+}$ Concentration Increase by Human BIR1 Via B Cell Receptor The cell which stably expresses FcR chimeric protein was allowed to incorporate Fura2-AM (final concentration: 5 μmol/l) (manufactured by Wako Pure Chemical Industries) at 37° C. for 30 minutes in the presence of 2.5 mmol/L of probenecid. After removing Fura2-AM, it was allowed to stand at 37° C. for 30 minutes in HEPES/Hanks' buffer containing 2.5 mmol/L of probenecid. After discarding the supernatant by centrifugation, the cells are suspended in HEPES/Hanks' buffer containing 2.5 mmol/L of probenecid at a density of $5 \times 10^6$ cells/mL and inoculated into a 96 well plate for $Ca^{2+}$ measurement at 100 μL/well. In a test in the absence of extracellular $Ca^{2+}$, the same operation was carried out using HEPES/Hanks' buffer containing 1 mmol/L EGTA/2.5 mmol/L probenecid prepared using $Ca^{2+}$-free Hanks' buffer. After standing at room temperature for 30 minutes, a fluorescence intensity ratio of 340 nm/380 nm was measured using Spectrofluorometer FDSS-4000 (manufactured by Hamamatsu Photonics), and a change in the intracellular $Ca^{2+}$ concentration was detected. After 30 seconds of the commencement of measurement, F(ab')$_2$ (33 μg/mL) of or intact (49.5 μg/mL) rabbit anti-mouse IgG (H+L) antibody (manufactured by Zymed) was added thereto in 10 μL/well portions.

As shown in FIG. 5, it was found that, when the BIR1 chimeric protein was crosslinked with BCR by the addition of the intact antibody, the BIR1 chimeric protein inhibited increase of intracellular $Ca^{2+}$ concentration, via BCR. On the other hand, increase of intracellular $Ca^{2+}$ concentration was not inhibited in the mutant in which intracellular tyrosine residues of BIR1 were replaced by phenylalanine residues. Additionally, the intracellular $Ca^{2+}$ concentration increase inhibition pattern of BIR1 was different from that of the positive control KIR2DL3. When intracellular $Ca^{2+}$ concentration increase inhibition patters of BIR1 and KIR2DL3 were compared in the absence of extracellular $Ca^{2+}$, KIR2DL3 completely inhibited increase of intracellular $Ca^{2+}$ concentration in the absence of extracellular $Ca^{2+}$, while BIR1 was unable to inhibit. BIR1 showed similar results of a known inhibitory receptor FcγRIIB (*Cell*, 90: 293-301 (1997)).

Based on the above results, it was shown that the BIR1 as a protein related to the present invention functions as an immunosuppressive receptor.

Example 7: Phosphorylation of Human BIR1 Intracellular Tyrosine Residue and Identification of Recruited Phosphatase, in Inhibitory Signal Transduction Examination was carried out on whether or not intracellular tyrosine residue is phosphorylated and a phosphatase is recruited when BIR1 is activated. With 30 μg/mL of F(ab')$_2$ of rabbit anti-mouse IgG (H+L) antibody or 45 μg/mL of intact antibody thereof (manufactured by Zymed), $3 \times 10^7$ cells of the FcR chimeric protein-stably expressing cell suspended in $Ca^{2+}$-containing HEPES/Hanks' buffer were stimulated at 37° C. for 3 minutes. Thereafter, the cells were lysed with a lysis buffer (1% NP-40, 50 mmol/L Tris-HCl, pH 8.0, 150 mmol/L NaCl, 50 mmol/L NaF, 10% glycerol, 1 mmol/L Na$_3$VO$_4$, 1 mol/L PMSF, proteinnase inhibitor cocktail tablet (manufactured by Roche Diagnostics)). The cell lysate was allowed to react with Protein A/G PLUS-Agarose (manufactured by Santacruz) to which a rat anti-mouse CD16/CD32 antibody (2.4G2) (manufactured by BD Pharmingen) is bound, at 4° C. for 5 hours or more. The FcR chimeric protein and binding molecules thereof are immunoprecipitated and then Western blotting was carried out in the usual way. The membrane was allowed to react with phosphotyrosine (4G10) (manufactured by Upstate) and primary antibodies for SHP-1, SHP-2 and SHIP-1 (manufactured by Santacruz), followed by the reaction with a horse radish peroxidase (HRP)-labeled secondary antibody (manufactured by Santacruz) to detect the bands by an ECL detection system (manufactured by Amersham Biosciences).

As a result, as shown in FIG. 6, intracellular tyrosine residue of BIR1 chimeric protein was phosphorylated when the BIR1 chimeric protein was crosslinked with BCR caused by the addition of the intact antibody. Additionally, SHP-1, SHP-2 and SHIP-1 were recruited into the intracellular region of BIR1 chimeric protein at that time. On the other hand, the phosphatase was not recruited in the mutant in which intracellular tyrosine residue of BIR1 was replaced by phenylalanine residue.

Example 8: Inhibition of Phosphorylation of Erk2 by Human BIR1

Examination was carried out whether or not BIR1 inhibits phosphorylation of the downstream signal transduction molecule via BCR. With 30 μg/mL of F(ab')$_2$ of rabbit anti-mouse IgG (H+L) antibody or 45 μg/mL of intact antibody thereof (manufactured by Zymed), 6×10$^6$ cells which stably express FcR chimeric protein suspended in Ca$^{2+}$-containing HEPES/Hanks' buffer were stimulated at 37° C. for 3 minutes. A cell lysate (500 ng/μl) was prepared using a lysing solution (Cell Lysis Kit; manufactured by BIO-RAD). Phosphorylation of each signal transduction molecule was determined using Bio-Plex Phospho 7-Plex Assay (manufactured by BIO-RAD).

As a result, as shown in FIG. 7, BIR1 chimeric protein inhibited BCR-mediated phosphorylation of Erk2 when the BIR1 chimeric protein was crosslinked with BCR by the addition of the intact antibody, similar to the case of KIR2DL3. On the other hand, the mutant in which intracellular tyrosine residue of BIR1 was replaced by phenylalanine residue did not inhibit phosphorylation of Erk2.

Example 9: Inhibition of Interleukin 2 (IL-2) Production by Human BIR1

Examination carried out on whether or not BIR1 inhibits BCR-mediated IL-2 production. After inoculation into 96 well plates, 1×10$^5$ cells which stably express the FcR chimeric protein were stimulated with 10 μg/mL of F(ab')$_2$ of rabbit anti-mouse IgG (H+L) antibody or 5 μg/mL of intact antibody thereof (manufactured by Zymed) at 37° C. for 24 hours. The amount of IL-2 in each culture supernatant was measured using Quantikine Immunoassay Mouse IL-2 ELISA Kit (manufactured by R & D Systems). As a result, as shown in FIG. 8, BIR1 chimeric protein inhibited BCR-mediated IL-2 production when the BIR1 chimeric protein was crosslinked with BCR by the addition of the intact antibody. On the other hand, the mutant in which intracellular tyrosine residue of BIR1 was replaced by phenylalanine residue did not inhibit IL-2 production. Additionally, as has been previously reported, KIR2DL3 also inhibited IL-2 production.

Example 10: Identification of ITIM Domain of Human BIR1 and Binding Phosphatase

The ITIM domain which is a sequence important for BIR1 in transmitting inhibitory signal and the binding phosphatase were identified. Peptides (Y3: Biotin-HSQELQ$^{313}$YATPVF (SEQ ID NO:23), Y5: Biotin-DSYKSG$^{336}$YVYSEL (SEQ ID NO:24), Y6: Biotin-YKSGYV$^{338}$YSELNF (SEQ ID NO:25)) containing intracellular tyrosine of BIR1 (SEQ ID NO:1) and their corresponding phosphorylated peptides (pY3: Biotin-HSQELQ$^{313}$(pY)ATPVF (SEQ ID NO:26), pY5: Biotin-DSYKSG$^{336}$(pY)VYSEL (SEQ ID NO:27), pY6: Biotin-YKSGYV$^{338}$(pY)SELNF (SEQ ID NO:28)) were synthesized (consigned to Sigma Genosys). A peptide containing the ITIM sequence of mouse PIR-B and its phosphorylated peptide (Y3: Biotin-ESQDVT$^{794}$YAQLCS (SEQ ID NO:29) and pY3: Biotin-ESQDVT$^{794}$(pY)AQLCS (SEQ ID NO:30)) were synthesized as positive controls. These peptides were connected to Protein A/G PLUS-Agarose (manufactured by Santacruz) via an anti-biotin antibody (manufactured by Sigma) and then allowed to react with a lysate of A20IIA1.6 cell at 4° C. for 2 hours. After immunoprecipitation, western blotting was carried out in the usual way. The membrane was allowed to react with primary antibodies for SHP-1, SHP-2 and SHIP-1 (manufactured by Santacruz), and then allowed to react with an (HRP)-labeled secondary antibody (manufactured by Santacruz), and the bands were detected using an ECL plus Western Blotting Detection System (manufactured by Amersham Biosciences).

As a result, as shown in FIG. 9, pY3 of BIR1 bound to SHP-1 and SHP-2, and pY6 bonded to SHP-1, SHP-2 and SHIP-1. On the other hand, pY5 did not bind to these phosphatases. Although a sequence which coincides with the consensus sequence of the conventional ITIM (I/V/L/SXYXXL/V) is not present in the intracellular region of BIR1, it was found that the 313th and 338th tyrosine residues of human BIR1 function as new ITIM.

Example 12: Preparation of Anti-Human BIR1 Antibody (1) Antigen Sensitization Using Solubilized Human BIR1L/Fc Chimeric Protein After mixing with TiterMax adjuvant (manufactured by Sigma), 60 μg portion of solubilized human BIR1L/Fc chimeric protein was administered into the intraperitoneal cavity of a BALB/c mouse. Two weeks after the initial administration, the antigen (60 μg) was mixed with TiterMax adjuvant and administered into the intraperitoneal cavity of the mouse. After about 10 days after the booster, the antigen (40 μg) was finally administered into the intraperitoneal cavity of the mouse. Three days thereafter, the spleen was harvested from the mouse.

(2) Preparation of Anti-Human BIR1 Monoclonal Antibody

Lymphocytes were separated from the spleen obtained in the aforementioned (1) and mixed with mouse myeloma P3U1 at a ratio of about 4:1 to carry out cell fusion using polyethylene glycol. Hybridomas were selected using RPMI 1640/15% FCS/HAT medium, and screening of hybridomas producing the objective antibody was carried out by an ELISA using the soluble human BIR1L/Fc chimeric protein and a flow cytometry using a CHO cell which stably express human BIR1L. Positive hybridomas were cloned by limiting dilution to obtain an anti-human BIR1 monoclonal antibody producer hybridoma. The hybridoma obtained by the manner was inoculated into the intraperitoneal cavity of a BALB/c mouse to collect peritoneal fluid 2 weeks or more thereafter. The antibody produced in the peritoneal fluid was purified using Prosep-G column (manufactured by Millipore) and the like.

As shown in FIG. 10, the thus prepared anti-human BIR1 monoclonal antibody recognized human BIR1 (in the drawing, Clone #170, #68, #95 and #31 represent respective clone of the anti-human BIR1 monoclonal antibody, and 2ndAb represents a negative control, and Anti-FLAG M2 represents a positive control).

(3) Preparation of Anti-Human BIR1 Polyclonal Antibody

Solubilized human BIR1L/Fc chimeric protein (100 µg/0.5 ml) was mixed with the same amount of complete Freund's adjuvant (manufactured by DIFCO) and administered under the dorsal skin of a rabbit. Two weeks thereafter, the antigen (100 µg/0.5 ml) was mixed with the same amount of incomplete Freund's adjuvant (manufactured by DIFCO) and administered under the dorsal skin of the rabbit. Two weeks thereafter, test blood was collected from the caudal vein, and increase in the antibody titer was verified by flow cytometry using CHO cells which express the human BIR1L. When the antibody titer was low, antiserum was prepared by further carrying out booster once or twice.

Example 13: Screening of a Compound which Changes Signal Transduction of Human BIR1

In the usual way, 10 µg/mL of rabbit anti-mouse IgG (H+L) antibody (manufactured by Zymed) and 10 µg/ml of the anti-human BIR1 monoclonal antibody prepared in Example 3 were immobilized on a 96 well plate. A tested compound (a low molecular compound, a peptide, an antibody or the like) was added thereto, and A20IIA1.6 cell which stably expresses the human BIR-1 was inoculated at a density of $1 \times 10^5$ cells/100 µL/well. After culturing at 37° C. for 24 hours, the amount of IL-2 in each culture supernatant was measured using Quantikine Immunoassay Mouse IL-2 ELISA Kit (manufactured by R & D Systems). A compound which reduces the amount of IL-2, or a compound which increases the same, in comparison with a negative control in which the tested compound was not added, is selected as the compound which changes signal transduction of human BIR1.

Example 14: Screening of a Compound which Controls Binding of Phosphatase

The phosphorylated peptides (Biotin-HSQELQ$^{313}$(pY) ATPVF (SEQ ID NO:26) or Biotin-YKSGYV$^{338}$(pY) SELNF (SEQ ID NO:28)) derived from 2 ITIM regions of human BIR1 were bound to a 96 well plate immobilized with an anti-biotin antibody (manufactured by Sigma). A tested compound (a low molecular compound, a peptide, an antibody or the like) was added thereto, and then a lysate of the A20IIA1.6 cell was added thereto, followed by incubation at 4° C. for 2 hours. After washing with PBS 5 times, primary antibodies for SHP-1, SHP-2 and SHIP-1 (manufactured by Santacruz) were added thereto. After allowing to react at room temperature for 2 hours and subsequent washing with PBS 5 times, an HRP-labeled secondary antibody (manufactured by Santacruz) was added thereto. After further carrying out the reaction at room temperature for 2 hours, the amount of phosphatase bound to the phosphorylated peptide was measured using a color developing kit for peroxidase (manufactured by Sumitomo Bakelite Co., Ltd.). A compound which reduces the amount of phosphatase, or a compound which increases the same, in comparison with a negative control in which the compound to be tested was not added, was selected.

Example 15: Screening of a Compound which Changes Expressed Amount of Human BIR1

A tested compound (a low molecular compound, a peptide, an antibody or the like) was added to human monocyte strain THP-1 cells ($1 \times 10^6$ cells/2 mL) in the presence or absence of LPS (1 µg/mL) and/or IFN-γ (100 ng/mL) and cultured at 37° C. for 24 hours. By extracting total RNA from respective cell, the RNA of BIR1 was determined by ABI PRISM 7000 Sequence Detection System (manufactured. by Applied Biosystems) using human BIR1-specific primers; 5'-CACAGCCATGGAAGTTGGAATC-3' (SEQ ID NO:15) and 5'-GAGTGTTTGGCCTCATCTTGG-3' (SEQ ID NO:16) and QuantiTect SYBR Green RT-PCR Kit (manufactured by QIAGEN). A compound which reduces the amount of RNA or a compound which increases the same in the presence of LPS and/or IFN-γ, in comparison with a negative control in which the tested compound was not added, was selected. Alternatively, a compound which reduces the amount of RNA or a compound which increases the same in the absence of LPS and IFN-γ, in comparison with a negative control in which the tested compound was not added, was selected.

INDUSTRIAL APPLICABILITY

The present invention is markedly useful in developing medicines. That is, an antagonist of the protein related to the present invention is useful in preventing and/or treating a cancer, an immunodeficiency disease or an infectious disease. Also, an antagonist of the protein related to the present invention is useful in preventing and/or treating an autoimmune disease, a rejection reaction after organ transplantation, an allergic disease or an inflammatory disease. The screening method of the present invention is useful in selecting an antagonist of the protein related to the present invention.

The protein of the present invention or a partial peptide thereof and an antibody for the protein of the present invention or a partial peptide thereof are useful in preventing and/or treating a cancer, an immunodeficiency disease or an infectious disease as an antagonist of the protein related to the present invention. Additionally, the protein of the present invention or a partial peptide thereof can be used as an antigen in producing the antibody for the protein of the present invention or a partial peptide thereof. The polynucleotide of the present invention can be used in producing the protein of the present invention or a partial peptide thereof.

BRIEF DESCRIPTION OF THE DRAWINGS

FIG. 3 shows a result of the analysis of changes in the expression of human BIR1 in autoimmune disease patient-derived monocytes and B cells (ND: normal donor, vWD: von Willebrand disease, SLE: systemic lupus erythematosus, RA: articular rheumatism, MS: multiple sclerosis, LA:

a disease having high value of lupus anticoagulation factor, TA: Takayasu arteritis, ITP: idiopathic thrombocytopenic purpura). *; $p<0.05$, ; $p<0.01$, *; $p<0.005$.

FIG. 4 shows expression level of FcR chimeric protein in cells which stably expresses FcR-hBIR1 (wt), FcR-hBIR1 (YWF) and FcR-hKIR2DL3.

Figure 1:
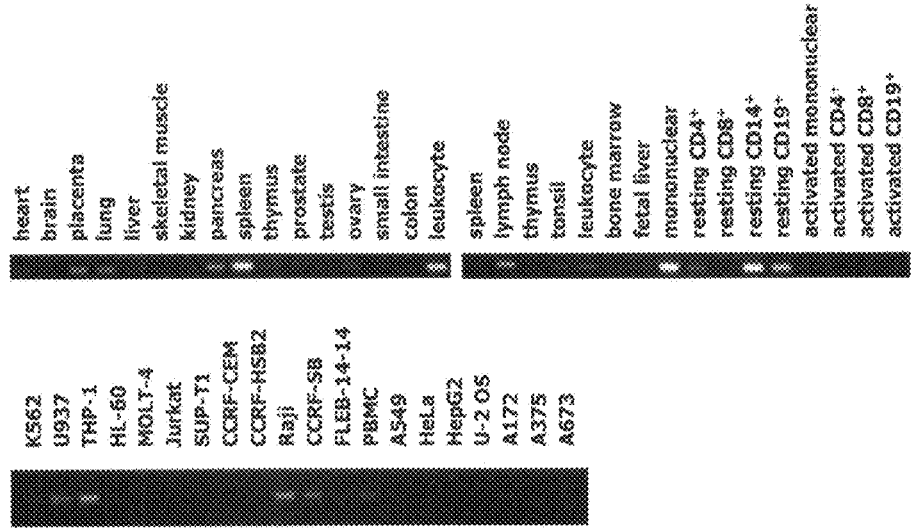
FIG. 1 shows expression level of the mRNA of BIR1 in human normal tissues, blood cells and cell lines.
Figure 2:
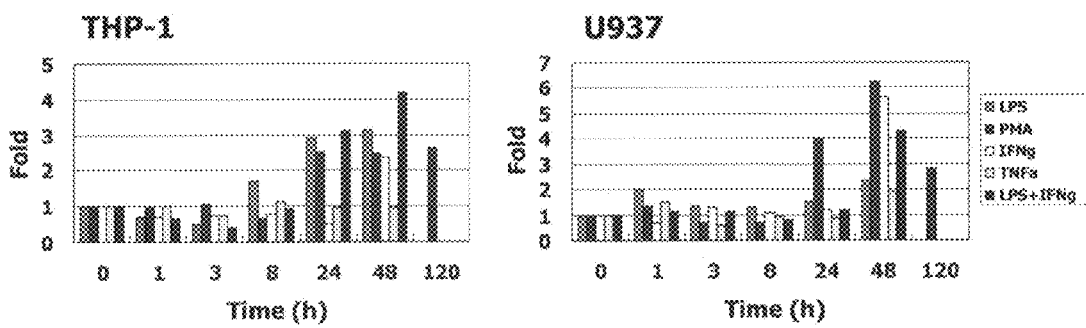
FIG. 2 shows changes in the expression of human BIR1 by various inflammation stimuli.
Figure 5:
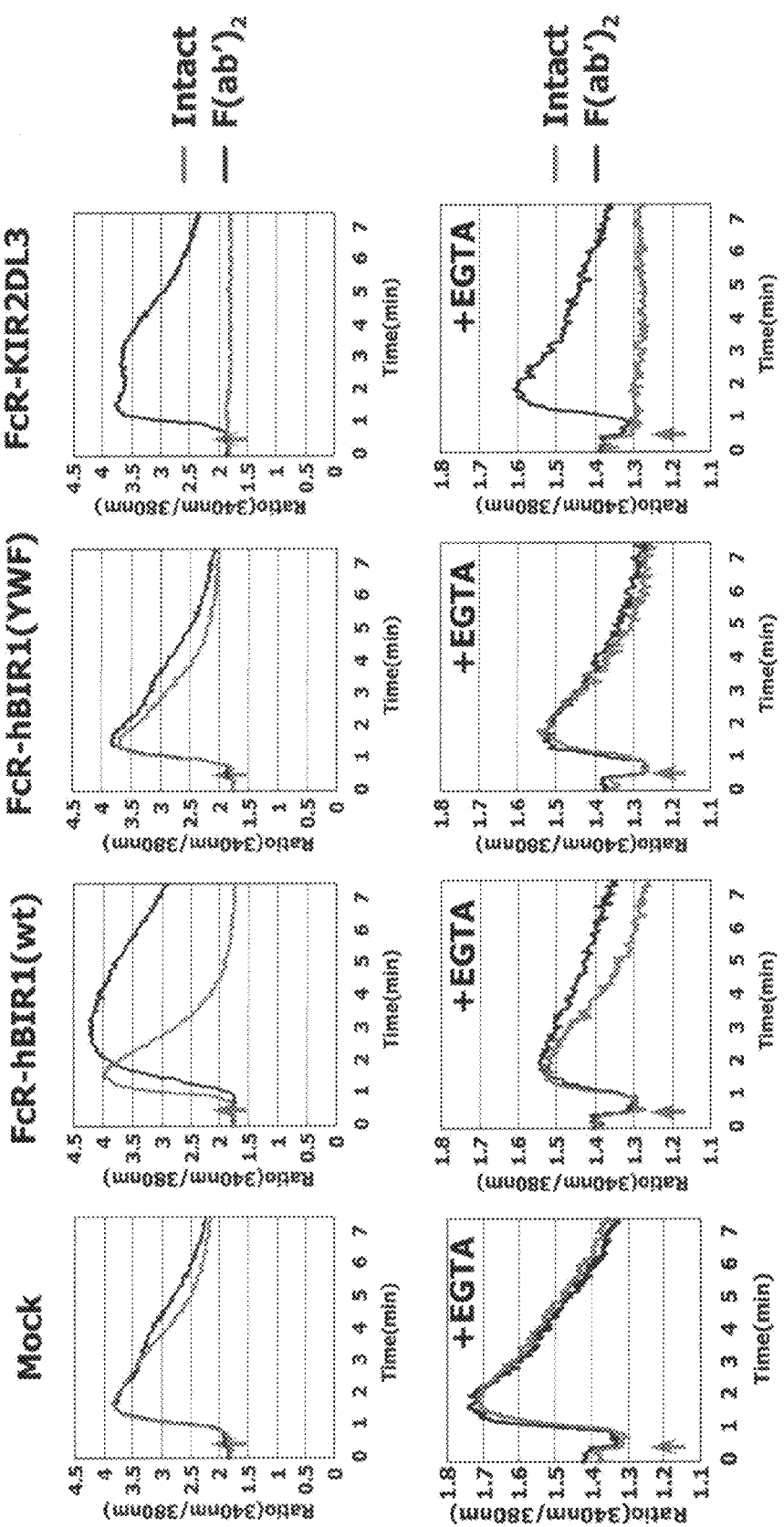

FIG. 5 shows inhibition of BCR-mediated increase of intracellular $Ca^{2+}$ concentration by human BIR1.

Figure 6:
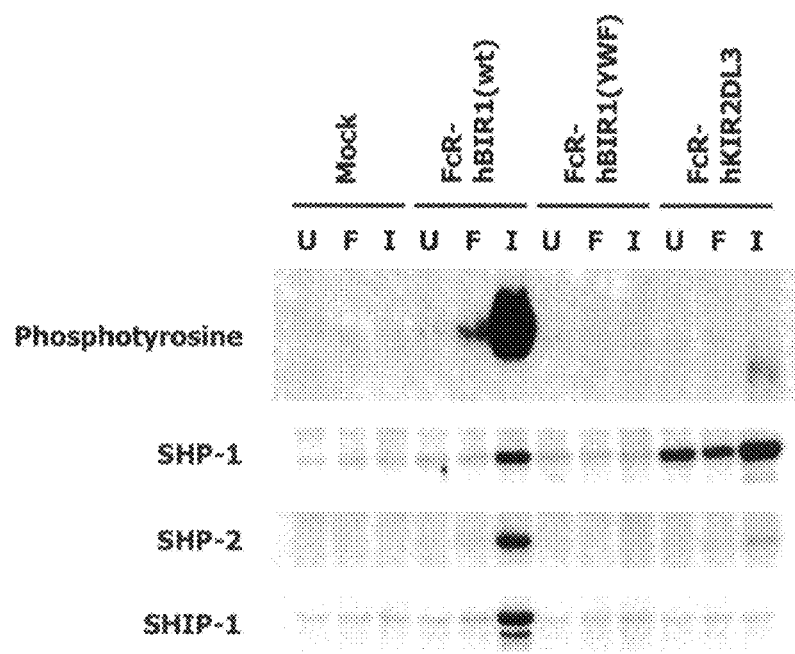

FIG. 6 shows phosphorylation of intracellular tyrosine residue of human BIR1 and recruited phosphatase, in inhibitory signal transduction (U: Unstimulated, F: F(ab')$_2$, I: Intact).

Figure 7:
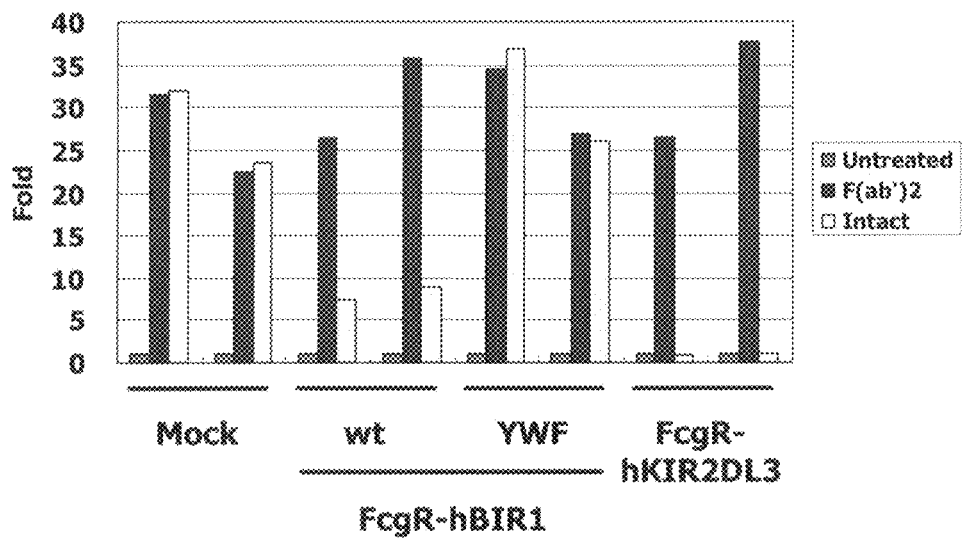

FIG. 7 shows inhibition of BCR-mediated phosphorylation of Erk2 by human BIR1.

Figure 8:
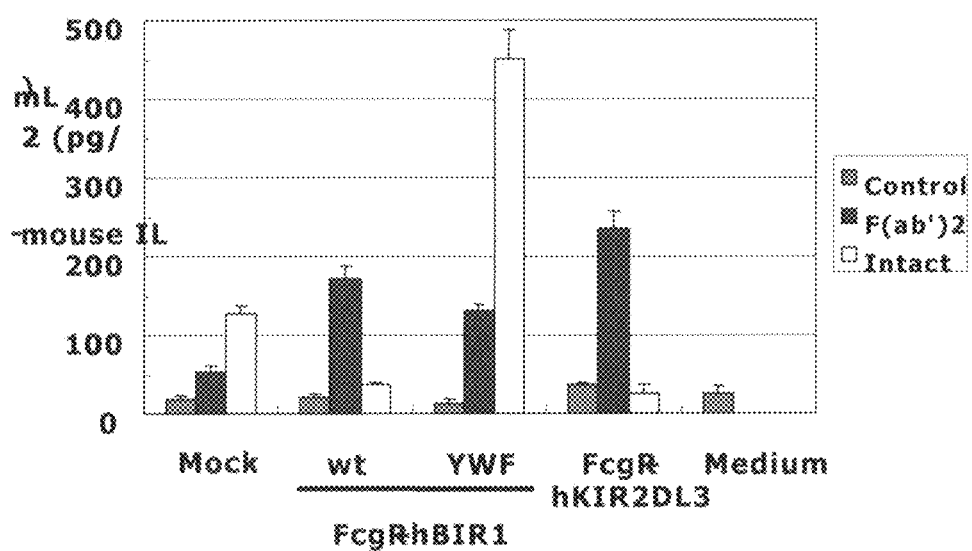

FIG. 8 shows inhibition of BCR-mediated production of IL-2 by human BIR1.

Figure 9:

FIG. 9 shows identification of ITIM domain of human BIR1 and binding phosphatase.

Figure 10:
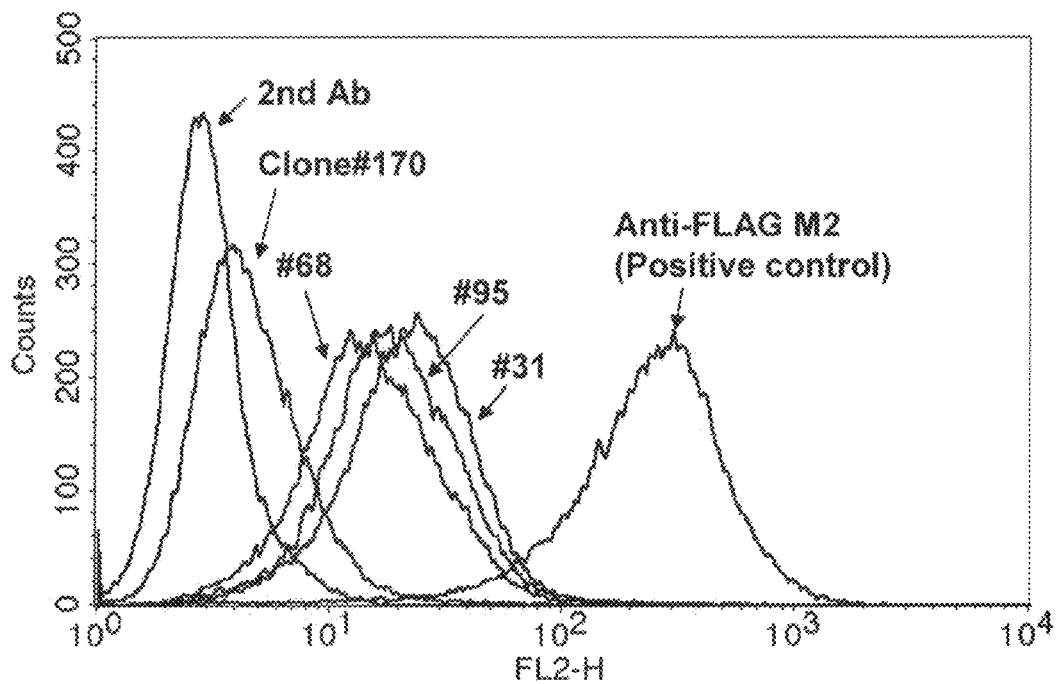

FIG. 10 shows antigen binding reaction of human BIR1 monoclonal antibody.

The invention claimed is:

1. A method of potentiating an immune response, comprising administering to a subject in need thereof an effective amount of an antagonist for a protein having the amino acid sequence set forth in any one of SEQ ID NOs: 1 to 6, wherein the antagonist is selected from (a) and (b):
   (a) an isolated polypeptide comprising an amino acid sequence selected from the group consisting of: residues 1-227 of SEQ ID NO: 1; residues 1-227 of SEQ ID NO: 2; residues 1-132 of SEQ ID NO: 3; residues 1-137 of SEQ ID NO: 4 and residues 1-132 of SEQ ID NO: 6; and
   (b) a monoclonal antibody against a protein having the amino acid sequence set forth in any one of SEQ ID NOs: 1 to 6.

2. The method according to claim 1, wherein the isolated polypeptide is fused to Fc domain of immunoglobulin.

3. The method according to claim 1, wherein the subject is a patient with cancer, immunodeficiency disease, or infection disease.

4. The method according to claim 3, wherein the cancer is cancer of stomach, large bowel cancer, metastatic sarcoma, central nervous system tumors, glioma, neuroblastoma, head and neck cancer, lingual cancer, gingival cancer, maxillary cancer, nasal cancer, nasal cavity cancer, laryngeal cancer and pharyngeal cancer, thyroid cancer, papillary carcinoma of thyroid, follicular carcinoma of thyroid, medullary carcinoma of thyroid and thyroid gland cancer, lung cancer, primary pulmonary carcinoma, squamous cell carcinoma, adenocarcinoma, alveolar carcinoma, large cell undifferentiated carcinoma, adenosquamous carcinoma, small cell undifferentiated carcinoma, mesothelioma, esophageal cancer, squamous carcinoma, adenocarcinoma, gastric cancer, adenocarcinoma, squamous cell carcinoma and carcinoid tumor, small intestinal cancer, duodenal cancer, liver cancer, primary cancer of liver, hepatoblastoma, pancreatic cancer, pancreas-gall bladder cancer, bladder cancer, renal pelvis and ureter cancer, ureteral transitional cell carcinoma, papillary carcinoma of urinary bladder, bladder transitional cell carcinoma, urethral squamous cell carcinoma, urethral adenocarcinoma, renal pelvic transitional cell carcinoma, prostate cancer, testicular tumor, renal cell carcinoma, breast cancer, mammary Paget disease, mammary sarcoma, melanoma, malignant melanoma, skin cancer, skin squamous cell carcinoma, skin basal cell carcinoma, skin Bowen disease, skin Paget disease, skin malignant melanoma, endometrial cancer, uterine intraepithelial carcinoma, adenocarcinoma of uterus, adenosquamous carcinoma of uterus, uterine body adenocarcinoma, uterine carcinosarcoma, invasive hydatidiform mole of uterus, malignant chorioepithelioma of uterus, uterine malignant melanoma, cervical cancer, cervical squamous cell carcinoma, ovarian cancer, hematopoietic tumor, malignant lymphoma, myeloma, acute myelocytic leukemia, acute promyelocytic leukemia, acute myelomonocytic leukemia, acute monocytic leukemia, acute lymphocytic leukemia, acute undifferentiated leukemia, chronic myeloid leukemia, chronic lymphocytic leukemia, adult T cell leukemia, multiple myeloma, primary macroglobulinemia, infantile leukemia, gastrointestinal malignant lymphoma, bone and soft tissue sarcoma, mesodermal mixed tumor, Wilms tumor, gastrocolic leiomyosarcoma, rhabdomyosarcoma, fibrosarcoma, osteosarcoma, chondrosarcoma, synovial sarcoma, myxosarcoma, liposarcoma and Ewing sarcoma.

5. The method according to claim 4, wherein the antagonist is administered in combination with a chemotherapeutic agent, an immune-stimulating cytokine or a cancer antigen.

6. The method according to claim 5, wherein the chemotherapeutic agent is selected from the group consisting of an alkylating agent, nitrosourea agent, metabolic antagonist, carcinostatic antibiotic, plant-derived alkaloid, topoisomerase inhibitor, hormone therapy agent, hormone antagonist, aromatase inhibitor, P glycoprotein inhibitor, platinum complex derivative, and immunotherapy agent.

7. The method according to claim 5, wherein the immune-stimulating cytokine is selected from the group consisting of GM-CSF, M-CSF, G-CSF, IL-1, IL-2, IL-3, IL-12, interferon-alpha, interferon-beta, and interferon-gamma.

8. The method according to claim 5, wherein the cancer antigen is selected from the group consisting of HLA-A1 or HLA-A2 restrictive peptide of malignant melanoma MAGE-1 or MAGE-3, MART-1, gp100, HER2/neu peptide of a mammary or ovarian carcinoma, MUC-1 peptide of an adenocarcinoma, and NY-ESO-1 of a metastatic carcinoma.

9. The method according to claim 3, wherein the immunodeficiency disease is acquired immunodeficiency syndrome caused by human immunodeficiency virus infection or immunodeficiency or primary immunodeficiency syndrome accompanied by serious disease.

10. The method according to claim 9, wherein the antagonist is administered in combination with an antiviral agent, an antibiotic preparation, an antibacterial agent, a visceral mycosis treating agent or a vaccine.

11. The method according to claim 3, wherein the infection disease is caused by hepatitis viruses, retrovirus, immunodeficiency viruses, T cell leukemia virus, T lympho-tropic virus, type 1 or type 2 herpes simplex virus, Epstein-Barr virus, cytomegalovirus, varicella-shingles virus, herpes viruses, polio virus, measles virus, rubella virus, Japanese encephalitis virus, mumps virus, influenza virus, common cold viruses, a virus that causes serious acute respiratory organ syndrome, Ebola virus, or Western Nile virus.

12. The method according to claim 11, wherein the antagonist is administered in combination with an antiviral agent, an antibiotic preparation, an antibacterial agent, a visceral mycosis treating agent or a vaccine.

13. The method according to claim 3, wherein the infection is caused by pathogenic protozoans, bacteria, or fungi.

14. The method according to claim 1, wherein the antagonistic monoclonal antibody is a chimeric antibody, humanized antibody, or human antibody.

15. The method according to claim 1, wherein the monoclonal antibody is a complete type antibody or a shortened type antibody.

16. The method according to claim 15, wherein the shortened type antibody is a F(ab')$_2$, Fab', Fab, or Fv fragment.

17. The method according to claim 1, wherein the antagonist is administered in combination with an anti-CD3 antibody, anti-CD28 antibody, or anti-CTLA-4 antibody.

* * * * *

SEQUENCE LISTING

```
<160> NUMBER OF SEQ ID NOS: 28

<210> SEQ ID NO 1
<211> LENGTH: 343
<212> TYPE: PRT
<213> ORGANISM: Homo sapiens

<400> SEQUENCE: 1

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110

Tyr Ser Arg Asp Phe Ser Phe Thr Ile Val Asp Pro Val Thr Ser Pro
        115                 120                 125

Val Leu Asn Ile Met Val Ile Gln Thr Glu Thr Asp Arg His Ile Thr
    130                 135                 140

Leu His Cys Leu Ser Val Asn Gly Ser Leu Pro Ile Asn Tyr Thr Phe
145                 150                 155                 160

Phe Glu Asn His Val Ala Ile Ser Pro Ala Ile Ser Lys Tyr Asp Arg
                165                 170                 175

Glu Pro Ala Glu Phe Asn Leu Thr Lys Lys Asn Pro Gly Glu Glu Glu
            180                 185                 190

Glu Tyr Arg Cys Glu Ala Lys Asn Arg Leu Pro Asn Tyr Ala Thr Tyr
        195                 200                 205

Ser His Pro Val Thr Met Pro Ser Thr Gly Gly Asp Ser Cys Pro Phe
    210                 215                 220

Cys Leu Lys Leu Leu Leu Pro Gly Leu Leu Leu Leu Leu Val Val Ile
225                 230                 235                 240

Ile Leu Ile Leu Ala Phe Trp Val Leu Pro Lys Tyr Lys Thr Arg Lys
                245                 250                 255

Ala Met Arg Asn Asn Val Pro Arg Asp Arg Gly Asp Thr Ala Met Glu
            260                 265                 270

Val Gly Ile Tyr Ala Asn Ile Leu Glu Lys Gln Ala Lys Glu Glu Ser
        275                 280                 285
```

```
Val Pro Glu Val Gly Ser Arg Pro Cys Val Ser Thr Ala Gln Asp Glu
    290                 295                 300

Ala Lys His Ser Gln Glu Leu Gln Tyr Ala Thr Pro Val Phe Gln Glu
305                 310                 315                 320

Val Ala Pro Arg Glu Gln Glu Ala Cys Asp Ser Tyr Lys Ser Gly Tyr
                325                 330                 335

Val Tyr Ser Glu Leu Asn Phe
                340

<210> SEQ ID NO 2
<211> LENGTH: 343
<212> TYPE: PRT
<213> ORGANISM: Homo sapiens

<400> SEQUENCE: 2

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
                20                  25                  30

Glu Phe Pro Ser Pro Cys Leu Asp Ser Lys Thr Lys Val Val Met Lys
                35                  40                  45

Gly Gln Asn Val Ser Met Phe Cys Ser His Lys Asn Lys Ser Leu Gln
50                  55                  60

Ile Thr Tyr Ser Leu Phe Arg Arg Lys Thr His Pro Gly Thr Gln Asp
65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
                100                 105                 110

Tyr Ser Arg Asp Phe Ser Phe Thr Ile Val Asp Pro Val Thr Ser Pro
                115                 120                 125

Val Leu Asn Ile Met Val Ile Gln Thr Glu Thr Asp Arg His Ile Thr
130                 135                 140

Leu His Cys Leu Ser Val Asn Gly Ser Leu Pro Ile Asn Tyr Thr Phe
145                 150                 155                 160

Phe Glu Asn His Val Ala Ile Ser Pro Ala Ile Ser Lys Tyr Asp Arg
                165                 170                 175

Glu Pro Ala Glu Phe Asn Leu Thr Lys Lys Asn Pro Gly Glu Glu Glu
                180                 185                 190

Glu Tyr Arg Cys Glu Ala Lys Asn Arg Leu Pro Asn Tyr Ala Thr Tyr
                195                 200                 205

Ser His Pro Val Thr Met Pro Ser Thr Gly Gly Asp Ser Cys Pro Phe
210                 215                 220

Cys Leu Lys Leu Leu Leu Pro Gly Leu Leu Leu Leu Val Val Ile
225                 230                 235                 240

Ile Leu Ile Leu Ala Phe Trp Val Leu Pro Lys Tyr Lys Thr Arg Lys
                245                 250                 255

Ala Met Arg Asn Asn Val Pro Arg Asp Arg Gly Asp Thr Ala Met Glu
                260                 265                 270

Val Gly Ile Tyr Ala Asn Ile Leu Glu Lys Gln Ala Lys Glu Glu Ser
                275                 280                 285

Val Pro Glu Val Gly Ser Arg Pro Cys Val Ser Thr Ala Gln Asp Glu
    290                 295                 300

Ala Lys His Ser Gln Glu Leu Gln Tyr Ala Thr Pro Val Phe Gln Glu
305                 310                 315                 320
```

Val Ala Pro Arg Glu Gln Glu Ala Cys Asp Ser Tyr Lys Ser Gly Tyr
            325                 330                 335

Val Tyr Ser Glu Leu Asn Phe
            340

<210> SEQ ID NO 3
<211> LENGTH: 248
<212> TYPE: PRT
<213> ORGANISM: Homo sapiens

<400> SEQUENCE: 3

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110

Tyr Ser Arg Asp Phe Ser Phe Thr Ile Val Gly Gly Asp Ser Cys Pro
        115                 120                 125

Phe Cys Leu Lys Leu Leu Leu Pro Gly Leu Leu Leu Leu Leu Val Val
    130                 135                 140

Ile Ile Leu Ile Leu Ala Phe Trp Val Leu Pro Lys Tyr Lys Thr Arg
145                 150                 155                 160

Lys Ala Met Arg Asn Asn Val Pro Arg Asp Arg Gly Asp Thr Ala Met
                165                 170                 175

Glu Val Gly Ile Tyr Ala Asn Ile Leu Glu Lys Gln Ala Lys Glu Glu
            180                 185                 190

Ser Val Pro Glu Val Gly Ser Arg Pro Cys Val Ser Thr Ala Gln Asp
        195                 200                 205

Glu Ala Lys His Ser Gln Glu Leu Gln Tyr Ala Thr Pro Val Phe Gln
    210                 215                 220

Glu Val Ala Pro Arg Glu Gln Glu Ala Cys Asp Ser Tyr Lys Ser Gly
225                 230                 235                 240

Tyr Val Tyr Ser Glu Leu Asn Phe
                245

<210> SEQ ID NO 4
<211> LENGTH: 253
<212> TYPE: PRT
<213> ORGANISM: Homo sapiens

<400> SEQUENCE: 4

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Asp Pro Val Thr Ser Pro Val Leu Asn Ile Met Val Ile Gln Thr Glu
        35                  40                  45

-continued

Thr Asp Arg His Ile Thr Leu His Cys Leu Ser Val Asn Gly Ser Leu
    50                  55                  60

Pro Ile Asn Tyr Thr Phe Phe Glu Asn His Val Ala Ile Ser Pro Ala
65                  70                  75                  80

Ile Ser Lys Tyr Asp Arg Glu Pro Ala Glu Phe Asn Leu Thr Lys Lys
                85                  90                  95

Asn Pro Gly Glu Glu Glu Glu Tyr Arg Cys Glu Ala Lys Asn Arg Leu
            100                 105                 110

Pro Asn Tyr Ala Thr Tyr Ser His Pro Val Thr Met Pro Ser Thr Gly
            115                 120                 125

Gly Asp Ser Cys Pro Phe Cys Leu Lys Leu Leu Pro Gly Leu Leu
    130                 135                 140

Leu Leu Leu Val Val Ile Ile Leu Ile Leu Ala Phe Trp Val Leu Pro
145                 150                 155                 160

Lys Tyr Lys Thr Arg Lys Ala Met Arg Asn Asn Val Pro Arg Asp Arg
                165                 170                 175

Gly Asp Thr Ala Met Glu Val Gly Ile Tyr Ala Asn Ile Leu Glu Lys
            180                 185                 190

Gln Ala Lys Glu Glu Ser Val Pro Glu Val Gly Ser Arg Pro Cys Val
        195                 200                 205

Ser Thr Ala Gln Asp Glu Ala Lys His Ser Gln Glu Leu Gln Tyr Ala
    210                 215                 220

Thr Pro Val Phe Gln Glu Val Ala Pro Arg Glu Gln Glu Ala Cys Asp
225                 230                 235                 240

Ser Tyr Lys Ser Gly Tyr Val Tyr Ser Glu Leu Asn Phe
                245                 250

<210> SEQ ID NO 5
<211> LENGTH: 158
<212> TYPE: PRT
<213> ORGANISM: Homo sapiens

<400> SEQUENCE: 5

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
                20                  25                  30

Gly Gly Asp Ser Cys Pro Phe Cys Leu Lys Leu Leu Leu Pro Gly Leu
            35                  40                  45

Leu Leu Leu Leu Val Val Ile Ile Leu Ile Leu Ala Phe Trp Val Leu
    50                  55                  60

Pro Lys Tyr Lys Thr Arg Lys Ala Met Arg Asn Asn Val Pro Arg Asp
65                  70                  75                  80

Arg Gly Asp Thr Ala Met Glu Val Gly Ile Tyr Ala Asn Ile Leu Glu
                85                  90                  95

Lys Gln Ala Lys Glu Glu Ser Val Pro Glu Val Gly Ser Arg Pro Cys
            100                 105                 110

Val Ser Thr Ala Gln Asp Glu Ala Lys His Ser Gln Glu Leu Gln Tyr
        115                 120                 125

Ala Thr Pro Val Phe Gln Glu Val Ala Pro Arg Glu Gln Glu Ala Cys
    130                 135                 140

Asp Ser Tyr Lys Ser Gly Tyr Val Tyr Ser Glu Leu Asn Phe
145                 150                 155

```
<210> SEQ ID NO 6
<211> LENGTH: 176
<212> TYPE: PRT
<213> ORGANISM: Homo sapiens

<400> SEQUENCE: 6

Met Trp Ser His Leu Asn Arg Leu Leu Phe Trp Ser Ile Phe Ser Ser
1               5                   10                  15

Val Thr Cys Arg Lys Ala Val Leu Asp Cys Glu Ala Met Lys Thr Asn
            20                  25                  30

Glu Phe Pro Ser Pro Cys Leu Asp Ser Lys Thr Lys Val Val Met Lys
        35                  40                  45

Gly Gln Asn Val Ser Met Phe Cys Ser His Lys Asn Lys Ser Leu Gln
    50                  55                  60

Ile Thr Tyr Ser Leu Phe Arg Arg Lys Thr His Leu Gly Thr Gln Asp
65                  70                  75                  80

Gly Lys Gly Glu Pro Ala Ile Phe Asn Leu Ser Ile Thr Glu Ala His
                85                  90                  95

Glu Ser Gly Pro Tyr Lys Cys Lys Ala Gln Val Thr Ser Cys Ser Lys
            100                 105                 110

Tyr Ser Arg Asp Phe Ser Phe Thr Ile Val Gly Gly Asp Ser Cys Pro
        115                 120                 125

Phe Cys Leu Lys Leu Leu Leu Pro Gly Leu Leu Leu Leu Val Val
    130                 135                 140

Ile Ile Leu Ile Leu Ala Phe Trp Val Leu Pro Lys Tyr Lys Thr Lys
145                 150                 155                 160

Ala Cys Asp Ser Tyr Lys Ser Gly Tyr Val Tyr Ser Glu Leu Asn Phe
                165                 170                 175

<210> SEQ ID NO 7
<211> LENGTH: 1029
<212> TYPE: DNA
<213> ORGANISM: Homo sapiens

<400> SEQUENCE: 7
atgtggagcc atttgaacag gctcctcttc tggagcatat tttcttctgt cacttgtaga      60
aaagctgtat tggattgtga ggcaatgaaa acaaatgaat tcccttctcc atgtttggac     120
tcaaagacta aggtggttat gaagggtcaa atgtatccta tgttttgttc ccataagaac     180
aaatcactgc agatcaccta ttcattgttt cgacgtaaga cacacctggg aacccaggat     240
ggaaaaggtg aacctgcgat ttttaaccta agcatcacag aagcccatga atcaggcccc     300
tacaaatgca agcccaagt accagctgt tcaaaataca gtcgtgactt cagcttcacg       360
attgtcgacc cggtgacttc cccagtgctg aacattatgg tcattcaaac agaaacagac     420
cgacatataa cattacattg cctctcagtc aatggctcgc tgcccatcaa ttacactttc     480
tttgaaaacc atgttgccat atccagct atttccaagt atgacaggga gcctgctgaa       540
tttaacttaa ccaagaagaa tcctggagaa gaggaagagt ataggtgtga agctaaaaac     600
agattgccta actatgcaac atacagtcac cctgtcacca tgcccctcaac aggcggagac   660 agctgtcctt tctgtctgaa gctactactt ccagggttat tactgttgct ggtggtgata    720
atcctaattc tggcttttttg ggtactgccc aaatacaaaa caagaaaagc tatgagaaat   780
aatgtgccca gggaccgtgg agacacagcc atggaagttg gaatctatgc aaatatcctt    840 gaaaacaag caaaggagga atctgtgcca gaagtgggat ccaggccgtg tgttt ccaca    900 gcccaagatg aggccaaaca ctcccaggag ctacagtatg ccaccccgt gttccaggag     960
```

```
gtggcaccaa gagagcaaga agcctgtgat tcttataaat ctggatatgt ctattctgaa   1020
ctcaacttc                                                           1029

<210> SEQ ID NO 8
<211> LENGTH: 1029
<212> TYPE: DNA
<213> ORGANISM: Homo sapiens

<400> SEQUENCE: 8
atgtggagcc atttgaacag gctcctcttc tggagcatat tttcttctgt cacttgtaga     60
aaagctgtat tggattgtga ggcaatgaaa acaaatgaat tcccttctcc atgtttggac    120
tcaaagacta aggtggttat gaagggtcaa aatgtatcta tgttttgttc ccataagaac    180
aaatcactgc agatcaccta ttcattgttt cgacgtaaga cacacccggg aacccaggat    240
ggaaaaggtg aacctgcgat ttttaaccta agcatcacag aagcccatga atcaggcccc    300
tacaaatgca agcccaagt taccagctgt tcaaaataca gtcgtgactt cagcttcacg     360
attgtcgacc cggtgacttc cccagtgctg aacattatgg tcattcaaac agaaacagac    420
cgacatataa cattcattg cctctcagtc aatggctcgc tgcccatcaa ttacactttc     480
tttgaaaacc atgttgccat atcaccagct atttccaagt atgacaggga gcctgctgaa    540
tttaacttaa ccaagaagaa tcctggagaa gaggaagagt ataggtgtga agctaaaaac    600
agattgccta actatgcaac atacagtcac cctgtcacca tgccctcaac aggcggagac    660
agctgtcctt tctgtctgaa gctactactt ccagggttat tactgttgct ggtggtgata    720
atcctaattc tggcttttg ggtactgccc aaatacaaaa caagaaaagc tatgagaaat     780
aatgtgccca gggaccgtgg agacacagcc atggaagttg aatctatgc aaatatcctt     840 gaaaaacaag caaggagga atctgtgcca gaagtgggat ccaggccgtg tgtttccaca    900
gcccaagatg aggccaaaca ctcccaggag ctacagtatg ccaccccgt gttccaggag     960 gtggcaccaa gagagcaaga agcctgtgat tcttataaat ctggatatgt ctattctgaa   1020
ctcaacttc                                                           1029

<210> SEQ ID NO 9
<211> LENGTH: 744
<212> TYPE: DNA
<213> ORGANISM: Homo sapiens

<400> SEQUENCE: 9
atgtggagcc atttgaacag gctcctcttc tggagcatat tttcttctgt cacttgtaga     60
aaagctgtat tggattgtga ggcaatgaaa acaaatgaat tcccttctcc atgtttggac    120
tcaaagacta aggtggttat gaagggtcaa aatgtatcta tgttttgttc ccataagaac    180
aaatcactgc agatcaccta ttcattgttt cgacgtaaga cacacctggg aacccaggat    240
ggaaaaggtg aacctgcgat ttttaaccta agcatcacag aagcccatga atcaggcccc    300
tacaaatgca agcccaagt taccagctgt tcaaaataca gtcgtgactt cagcttcacg     360
attgtcggcg gagacagctg tccttttctgt ctgaagctac tacttccagg gttattactg    420
ttgctggtgg tgataatcct aattctggct ttttgggtac tgcccaaata caaaacaaga    480
aaagctatga aaataatgt gcccagggac cgtggagaca cagccatgga agttggaatc    540
tatgcaaata tccttgaaaa acaagcaaag gaggaatctg tgccagaagt gggatccagg    600
ccgtgtgttt ccacagccca agatgaggcc aaacactccc aggagctaca gtatgccacc    660
```

| cccgtgttcc aggaggtggc accaagagag caagaagcct gtgattctta taaatctgga | 720 |
| tatgtctatt ctgaactcaa cttc | 744 |

<210> SEQ ID NO 10
<211> LENGTH: 759
<212> TYPE: DNA
<213> ORGANISM: Homo sapiens

<400> SEQUENCE: 10

| atgtggagcc atttgaacag gctcctcttc tggagcatat tttcttctgt cacttgtaga | 60 |
| aaagctgtat tggattgtga ggcaatgaaa acaaatgacc cggtgacttc cccagtgctg | 120 |
| aacattatgg tcattcaaac agaaacagac cgacatataa cattacattg cctctcagtc | 180 |
| aatggctcgc tgcccatcaa ttacactttc tttgaaaacc atgttgccat atcaccagct | 240 |
| atttccaagt atgacaggga gcctgctgaa tttaacttaa ccaagaagaa tcctggagaa | 300 |
| gaggaagagt ataggtgtga agctaaaaac agattgccta actatgcaac atacagtcac | 360 |
| cctgtcacca tgcctcaac aggcggagac agctgtcctt tctgtctgaa gctactactt | 420 |
| ccagggttat tactgttgct ggtggtgata atcctaattc tggcttttg ggtactgccc | 480 |
| aaatacaaaa caagaaaagc tatgagaaat aatgtgccca gggaccgtgg agacacagcc | 540 |
| atggaagttg gaatctatgc aaatatcctt gaaaaacaag caaggagga atctgtgcca | 600 |
| gaagtgggat ccaggccgtg tgtttccaca gcccaagatg aggccaaaca ctcccaggag | 660 |
| ctacagtatg ccaccccgt gttccaggag gtggcaccaa gagagcaaga agcctgtgat | 720 |
| tcttataaat ctggatatgt ctattctgaa ctcaacttc | 759 |

<210> SEQ ID NO 11
<211> LENGTH: 474
<212> TYPE: DNA
<213> ORGANISM: Homo sapiens

<400> SEQUENCE: 11

| atgtggagcc atttgaacag gctcctcttc tggagcatat tttcttctgt cacttgtaga | 60 |
| aaagctgtat tggattgtga ggcaatgaaa acaaatggcg agacagctg tcctttctgt | 120 |
| ctgaagctac tacttccagg gttattactg ttgctggtgg tgataatcct aattctggct | 180 |
| ttttgggtac tgcccaaata caaaacaaga aaagctatga gaataatgt gcccagggac | 240 |
| cgtggagaca cagccatgga agttggaatc tatgcaaata tccttgaaaa acaagcaaag | 300 |
| gaggaatctg tgccagaagt gggatccagg ccgtgtgttt ccacagccca agatgaggcc | 360 |
| aaacactccc aggagctaca gtatgccacc cccgtgttcc aggaggtggc accaagagag | 420 |
| caagaagcct gtgattctta taaatctgga tatgtctatt ctgaactcaa cttc | 474 |

<210> SEQ ID NO 12
<211> LENGTH: 528
<212> TYPE: DNA
<213> ORGANISM: Homo sapiens

<400> SEQUENCE: 12

| atgtggagcc atttgaacag gctcctcttc tggagcatat tttcttctgt cacttgtaga | 60 |
| aaagctgtat tggattgtga ggcaatgaaa acaaatgaat tcccttctcc atgtttggac | 120 |
| tcaaagacta aggtggttat gaagggtcaa aatgtatcta tgttttgttc ccataagaac | 180 |
| aaatcactgc agatcaccta ttcattgttt cgacgtaaga cacacctggg aacccaggat | 240 |
| ggaaaaggtg aacctgcgat ttttaaccta agcatcacag aagcccatga atcaggcccc | 300 |

```
tacaaatgca aagcccaagt taccagctgt tcaaaataca gtcgtgactt cagcttcacg        360
attgtcggcg agacagctg tcctttctgt ctgaagctac tacttccagg gttattactg         420
ttgctggtgg tgataatcct aattctggct ttttgggtac tgcccaaata caaaacaaaa        480
gcctgtgatt cttataaatc tggatatgtc tattctgaac tcaacttc                     528

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 13
gaacaggctc ctcttctgga g                                                   21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 14
ggttcacctt ttccatcctg g                                                   21

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 15
cacagccatg gaagttggaa tc                                                  22

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 16
gagtgtttgg cctcatcttg g                                                   21

<210> SEQ ID NO 17
<211> LENGTH: 615
<212> TYPE: DNA
<213> ORGANISM: Artificial Sequence
<220> FEATURE:
<223> OTHER INFORMATION: Synthetic human BIR1 cDNA fragment

<400> SEQUENCE: 17
gcctgctgaa tttaacttaa ccaagaagaa tcctggagaa gaggaagagt ataggtgtga        60
agctaaaaac agattgccta actatgcaac atacagtcac cctgtcacca tgccctcaac       120
aggcggagac agctgtcctt tctgtctgaa gctactactt ccagggttat tactgttgct       180
ggtggtgata atcctaattc tggcttttg ggtactgccc aaatacaaaa caagaaaagc        240
tatgagaaat aatgtgccca gggaccgtgg agacacagcc atggaagttg gaatctatgc       300
aaatatcctt gaaaacaag caaggagga atctgtgcca gaagtgggat ccaggccgtg         360
```

```
tgtttccaca gcccaagatg aggccaaaca ctcccaggag ctacagtatg ccacccccgt      420
gttccaggag gtggcaccaa gagagcaaga agcctgtgat tcttataaat ctggatatgt      480
ctattctgaa ctcaacttct gaaatttaca gaaacaaact acatctcagg gtaagatgct      540
ttttatgaag ctgatttcca tgaacaaaaa gcaaacttga ggctgaggcg ggtggatcac      600
agggtcagga gatca                                                      615
```

<210> SEQ ID NO 18
<211> LENGTH: 27
<212> TYPE: DNA
<213> ORGANISM: Artificial Sequence
<220> FEATURE:
<223> OTHER INFORMATION: Synthetic oligonucleotide primer

<400> SEQUENCE: 18

```
atgtggagcc atttgaacag gctcctc                                          27
```

<210> SEQ ID NO 19
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 19

```
tcagaagttg agttcagaat agac                                             24
```

<210> SEQ ID NO 20
<211> LENGTH: 345
<212> TYPE: PRT
<213> ORGANISM: Artificial Sequence
<220> FEATURE:
<223> OTHER INFORMATION: Synthetic FcRIIB-human BIR1 chimeric protein

<400> SEQUENCE: 20

```
Met Gly Ile Leu Pro Phe Leu Leu Ile Pro Met Glu Ser Asn Trp Thr
1               5                   10                  15

Val His Val Phe Ser Arg Thr Leu Cys His Met Leu Leu Trp Thr Ala
            20                  25                  30

Val Leu Asn Leu Ala Ala Gly Thr His Asp Leu Pro Lys Ala Val Val
        35                  40                  45

Lys Leu Glu Pro Pro Trp Ile Gln Val Leu Lys Glu Asp Thr Val Thr
    50                  55                  60

Leu Thr Cys Glu Gly Thr His Asn Pro Gly Asn Ser Ser Thr Gln Trp
65                  70                  75                  80

Phe His Asn Gly Arg Ser Ile Arg Ser Gln Val Gln Ala Ser Tyr Thr
                85                  90                  95

Phe Lys Ala Thr Val Asn Asp Ser Gly Glu Tyr Arg Cys Gln Met Glu
            100                 105                 110

Gln Thr Arg Leu Ser Asp Pro Val Asp Leu Gly Val Ile Ser Asp Trp
        115                 120                 125

Leu Leu Leu Gln Thr Pro Gln Leu Val Phe Leu Glu Gly Glu Thr Ile
    130                 135                 140

Thr Leu Arg Cys His Ser Trp Arg Asn Lys Leu Leu Asn Arg Ile Ser
145                 150                 155                 160

Phe Phe His Asn Glu Lys Ser Val Arg Tyr His His Tyr Ser Ser Asn
                165                 170                 175

Phe Ser Ile Pro Lys Ala Asn His Ser His Ser Gly Asp Tyr Tyr Cys
            180                 185                 190
```

Lys Gly Ser Leu Gly Arg Thr Leu His Gln Ser Lys Pro Val Thr Ile
            195                 200                 205

Thr Val Gln Gly Pro Lys Ser Arg Ser Leu Pro Val Leu Thr Ile
210                 215                 220

Val Ala Val Thr Gly Ile Ala Val Ala Ala Ile Val Ile Ile Leu
225                 230                 235                 240

Val Ser Leu Val Tyr Leu Lys Lys Lys Gln Val Pro Lys Tyr Lys Thr
                245                 250                 255

Arg Lys Ala Met Arg Asn Asn Val Pro Arg Asp Arg Gly Asp Thr Ala
            260                 265                 270

Met Glu Val Gly Ile Tyr Ala Asn Ile Leu Glu Lys Gln Ala Lys Glu
            275                 280                 285

Glu Ser Val Pro Glu Val Gly Ser Arg Pro Cys Val Ser Thr Ala Gln
290                 295                 300

Asp Glu Ala Lys His Ser Gln Glu Leu Gln Tyr Ala Thr Pro Val Phe
305                 310                 315                 320

Gln Glu Val Ala Pro Arg Glu Gln Glu Ala Cys Asp Ser Tyr Lys Ser
                325                 330                 335

Gly Tyr Val Tyr Ser Glu Leu Asn Phe
            340                 345

<210> SEQ ID NO 21
<211> LENGTH: 345
<212> TYPE: PRT
<213> ORGANISM: Artificial Sequence
<220> FEATURE:
<223> OTHER INFORMATION: Synthetic FcRIIB-human BIR1 chimeric protein

<400> SEQUENCE: 21

Met Gly Ile Leu Pro Phe Leu Leu Ile Pro Met Glu Ser Asn Trp Thr
1               5                   10                  15

Val His Val Phe Ser Arg Thr Leu Cys His Met Leu Leu Trp Thr Ala
            20                  25                  30

Val Leu Asn Leu Ala Ala Gly Thr His Asp Leu Pro Lys Ala Val Val
        35                  40                  45

Lys Leu Glu Pro Pro Trp Ile Gln Val Leu Lys Glu Asp Thr Val Thr
50                  55                  60

Leu Thr Cys Glu Gly Thr His Asn Pro Gly Asn Ser Ser Thr Gln Trp
65                  70                  75                  80

Phe His Asn Gly Arg Ser Ile Arg Ser Gln Val Gln Ala Ser Tyr Thr
                85                  90                  95

Phe Lys Ala Thr Val Asn Asp Ser Gly Glu Tyr Arg Cys Gln Met Glu
            100                 105                 110

Gln Thr Arg Leu Ser Asp Pro Val Asp Leu Gly Val Ile Ser Asp Trp
        115                 120                 125

Leu Leu Leu Gln Thr Pro Gln Leu Val Phe Leu Glu Gly Glu Thr Ile
130                 135                 140

Thr Leu Arg Cys His Ser Trp Arg Asn Lys Leu Leu Asn Arg Ile Ser
145                 150                 155                 160

Phe Phe His Asn Glu Lys Ser Val Arg Tyr His His Tyr Ser Ser Asn
                165                 170                 175

Phe Ser Ile Pro Lys Ala Asn His Ser His Ser Gly Asp Tyr Tyr Cys
            180                 185                 190

Lys Gly Ser Leu Gly Arg Thr Leu His Gln Ser Lys Pro Val Thr Ile
        195                 200                 205

```
Thr Val Gln Gly Pro Lys Ser Ser Arg Ser Leu Pro Val Leu Thr Ile
        210                 215                 220

Val Ala Ala Val Thr Gly Ile Ala Val Ala Ala Ile Val Ile Ile Leu
225                 230                 235                 240

Val Ser Leu Val Tyr Leu Lys Lys Lys Gln Val Pro Lys Phe Lys Thr
                245                 250                 255

Arg Lys Ala Met Arg Asn Asn Val Pro Arg Asp Arg Gly Asp Thr Ala
                260                 265                 270

Met Glu Val Gly Ile Phe Ala Asn Ile Leu Glu Lys Gln Ala Lys Glu
                275                 280                 285

Glu Ser Val Pro Glu Val Gly Ser Arg Pro Cys Val Ser Thr Ala Gln
        290                 295                 300

Asp Glu Ala Lys His Ser Gln Glu Leu Gln Phe Ala Thr Pro Val Phe
305                 310                 315                 320

Gln Glu Val Ala Pro Arg Glu Gln Glu Ala Cys Asp Ser Phe Lys Ser
                325                 330                 335

Gly Phe Val Phe Ser Glu Leu Asn Phe
                340                 345

<210> SEQ ID NO 22
<211> LENGTH: 330
<212> TYPE: PRT
<213> ORGANISM: Artificial Sequence
<220> FEATURE:
<223> OTHER INFORMATION: Synthetic FcR-human KIR2DL3 chimeric protein

<400> SEQUENCE: 22

Met Gly Ile Leu Pro Phe Leu Leu Ile Pro Met Glu Ser Asn Trp Thr
1               5                   10                  15

Val His Val Phe Ser Arg Thr Leu Cys His Met Leu Leu Trp Thr Ala
                20                  25                  30

Val Leu Asn Leu Ala Ala Gly Thr His Asp Leu Pro Lys Ala Val Val
            35                  40                  45

Lys Leu Glu Pro Pro Trp Ile Gln Val Leu Lys Glu Asp Thr Val Thr
50                  55                  60

Leu Thr Cys Glu Gly Thr His Asn Pro Gly Asn Ser Ser Thr Gln Trp
65                  70                  75                  80

Phe His Asn Gly Arg Ser Ile Arg Ser Gln Val Gln Ala Ser Tyr Thr
                85                  90                  95

Phe Lys Ala Thr Val Asn Asp Ser Gly Glu Tyr Arg Cys Gln Met Glu
                100                 105                 110

Gln Thr Arg Leu Ser Asp Pro Val Asp Leu Gly Val Ile Ser Asp Trp
            115                 120                 125

Leu Leu Leu Gln Thr Pro Gln Leu Val Phe Leu Glu Gly Glu Thr Ile
        130                 135                 140

Thr Leu Arg Cys His Ser Trp Arg Asn Lys Leu Leu Asn Arg Ile Ser
145                 150                 155                 160

Phe Phe His Asn Glu Lys Ser Val Arg Tyr His His Tyr Ser Ser Asn
                165                 170                 175

Phe Ser Ile Pro Lys Ala Asn His Ser His Ser Gly Asp Tyr Tyr Cys
            180                 185                 190

Lys Gly Ser Leu Gly Arg Thr Leu His Gln Ser Lys Pro Val Thr Ile
        195                 200                 205

Thr Val Gln Gly Pro Lys Ser Ser Arg Ser Leu Pro Val Leu Thr Ile
        210                 215                 220
```

Val Ala Val Thr Gly Ile Ala Val Ala Ile Val Ile Leu
225                 230                 235                 240

Val Ser Leu Val Tyr Leu His Arg Trp Cys Cys Asn Lys Lys Asn Ala
            245                 250                 255

Val Val Met Asp Gln Glu Pro Ala Gly Asn Arg Thr Val Asn Arg Glu
        260                 265                 270

Asp Ser Asp Glu Gln Asp Pro Gln Glu Val Thr Tyr Ala Gln Leu Asn
        275                 280                 285

His Cys Val Phe Thr Gln Arg Lys Ile Ser Arg Pro Ser Gln Arg Pro
        290                 295                 300

Lys Thr Pro Pro Thr Asp Ile Ile Val Tyr Thr Glu Leu Pro Asn Ala
305                 310                 315                 320

Glu Pro Asp Tyr Lys Asp Asp Asp Lys
                325                 330

<210> SEQ ID NO 23
<211> LENGTH: 12
<212> TYPE: PRT
<213> ORGANISM: Artificial Sequence
<220> FEATURE:
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation

<400> SEQUENCE: 23

His Ser Gln Glu Leu Gln Tyr Ala Thr Pro Val Phe
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation

<400> SEQUENCE: 24

Asp Ser Tyr Lys Ser Gly Tyr Val Tyr Ser Glu Leu
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation

<400> SEQUENCE: 25

Tyr Lys Ser Gly Tyr Val Tyr Ser Glu Leu Asn Phe
1               5                   10

<210> SEQ ID NO 26
<211> LENGTH: 12
<212> TYPE: PRT
<213> ORGANISM: Artificial Sequence
<220> FEATURE:

```
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation
<220> FEATURE:
<221> NAME/KEY: PHOSPHORYLATION
<222> LOCATION: (7)..(7)

<400> SEQUENCE: 26

His Ser Gln Glu Leu Gln Tyr Ala Thr Pro Val Phe
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation
<220> FEATURE:
<221> NAME/KEY: PHOSPHORYLATION
<222> LOCATION: (7)..(7)

<400> SEQUENCE: 27

Asp Ser Tyr Lys Ser Gly Tyr Val Tyr Ser Glu Leu
1               5                   10

<210> SEQ ID NO 28
<211> LENGTH: 12
<212> TYPE: PRT
<213> ORGANISM: Artificial
<220> FEATURE:
<223> OTHER INFORMATION: Synthetic BIR1 oligopeptide
<220> FEATURE:
<221> NAME/KEY: MOD_RES
<222> LOCATION: (1)..(1)
<223> OTHER INFORMATION: Biotinylation
<220> FEATURE:
<221> NAME/KEY: PHOSPHORYLATION
<222> LOCATION: (7)..(7)

<400> SEQUENCE: 28

Tyr Lys Ser Gly Tyr Val Tyr Ser Glu Leu Asn Phe
1               5                   10
```